(12) United States Patent
Coppeta et al.

(10) Patent No.: US 12,247,190 B2
(45) Date of Patent: *Mar. 11, 2025

(54) BI-LAYER MULTI-WELL CELL CULTURE PLATFORM

(71) Applicant: The Charles Stark Draper Laboratory, Inc., Cambridge, MA (US)

(72) Inventors: Jonathan R. Coppeta, Windham, NH (US); Joseph L Charest, Cambridge, MA (US); Else M. Vedula, Brookline, MA (US); Jeffrey T. Borenstein, Newton, MA (US); Abigail June Spencer, Boston, MA (US); Brett C. Isenberg, West Newton, MA (US)

(73) Assignee: The Charles Stark Draper Laboratory, Inc., Cambridge, MD (US)

( * ) Notice: Subject to any disclaimer, the term of this patent is extended or adjusted under 35 U.S.C. 154(b) by 990 days.

This patent is subject to a terminal disclaimer.

(21) Appl. No.: 17/240,634

(22) Filed: Apr. 26, 2021

(65) Prior Publication Data
US 2021/0238526 A1 Aug. 5, 2021

Related U.S. Application Data

(63) Continuation of application No. 15/819,986, filed on Nov. 21, 2017, now Pat. No. 11,001,796.
(Continued)

(51) Int. Cl.
*C12M 1/12* (2006.01)
*C12M 1/00* (2006.01)
(Continued)

(52) U.S. Cl.
CPC ............ *C12M 25/04* (2013.01); *C12M 21/08* (2013.01); *C12M 23/12* (2013.01); *C12M 23/16* (2013.01);
(Continued)

(58) Field of Classification Search
CPC ..... B01L 3/5027; C12M 21/08; C12M 23/16; C12M 25/04; C12N 5/069; G16H 50/20; G16H 50/50; G16H 70/60
See application file for complete search history.

(56) References Cited

U.S. PATENT DOCUMENTS 6,729,352 B2   5/2004   O'Connor et al.
9,249,387 B2   2/2016   Cuiffi et al.
(Continued)

FOREIGN PATENT DOCUMENTS

AU   2012223526 B2   3/2017
AU   2015289999 A2   3/2017
(Continued)

OTHER PUBLICATIONS

Office Action issued Sep. 27, 2021 in European Patent Application No. 17817960.2.
(Continued)

*Primary Examiner* — Jill A Warden
*Assistant Examiner* — Dwayne K Handy
(74) *Attorney, Agent, or Firm* — Brooks Kushman P.C.

(57) ABSTRACT

The methods and systems described herein provide a cell culture platform with an array of tissue modeling environments and dynamic control of fluid flow. The cell culture platform includes an array of wells that are fluidically coupled by microchannel structures. The dynamically controlled flow of fluid interacts with cells grown within the microchannels.

13 Claims, 14 Drawing Sheets

Related U.S. Application Data

(60) Provisional application No. 62/425,658, filed on Nov. 23, 2016.

(51) Int. Cl.

| | | |
|---|---|---|
| *C12M 1/32* | (2006.01) | |
| *C12M 1/34* | (2006.01) | |
| *C12M 1/36* | (2006.01) | |
| *C12M 1/42* | (2006.01) | |
| *C12M 3/00* | (2006.01) | |
| *C12M 3/06* | (2006.01) | |
| *C12N 5/071* | (2010.01) | |
| *G01N 33/50* | (2006.01) | |

(52) U.S. Cl.
CPC ............ *C12M 25/02* (2013.01); *C12M 29/00* (2013.01); *C12M 35/08* (2013.01); *C12M 41/00* (2013.01); *C12M 41/48* (2013.01); *C12N 5/0686* (2013.01); *C12N 5/069* (2013.01); *G01N 33/5082* (2013.01); *C12N 2533/30* (2013.01); *C12N 2535/00* (2013.01)

(56) References Cited

U.S. PATENT DOCUMENTS

| | | | |
|---|---|---|---|
| 9,528,082 | B2 | 12/2016 | Cuiffi et al. |
| 9,599,604 | B2 | 3/2017 | Mcfetridge |
| 2010/0240086 | A1 | 9/2010 | Kashanin et al. |
| 2013/0059322 | A1 | 3/2013 | Hung et al. |
| 2013/0084632 | A1 | 4/2013 | Legallais et al. |
| 2014/0356849 | A1 | 12/2014 | Wikswo et al. |
| 2014/0370598 | A1 | 12/2014 | Colton et al. |
| 2015/0004077 | A1* | 1/2015 | Wikswo ............... C12M 41/00 422/502 |
| 2015/0298123 | A1 | 10/2015 | Block, III et al. |
| 2016/0040112 | A1 | 2/2016 | Coppeta et al. |
| 2016/0145553 | A1 | 5/2016 | Cuiffi et al. |
| 2016/0145555 | A1 | 5/2016 | Ingber et al. |
| 2016/0175840 | A1 | 6/2016 | Ingber et al. |
| 2016/0220997 | A1 | 8/2016 | Mescher et al. |
| 2016/0326477 | A1 | 11/2016 | Fernandez-Alcon et al. |
| 2017/0058257 | A1 | 3/2017 | Levner et al. |
| 2017/0065976 | A1* | 3/2017 | Varma ................... F04B 49/065 |
| 2018/0346867 | A1* | 12/2018 | Oliver ................... C12M 23/16 |

FOREIGN PATENT DOCUMENTS

| | | |
|---|---|---|
| CN | 105308452 A | 2/2016 |
| EP | 3041926 A1 | 7/2016 |
| EP | 3126484 A1 | 2/2017 |
| WO | 2012/118799 A2 | 9/2012 |
| WO | 2015/153451 A1 | 10/2015 |
| WO | 2016049365 A1 | 3/2016 |
| WO | 2016065004 A1 | 4/2016 |
| WO | 2016127009 A1 | 8/2016 |
| WO | 2017003546 A2 | 1/2017 |
| WO | 2017027838 A1 | 2/2017 |

OTHER PUBLICATIONS

International Search Report and Written Opinion mailed Feb. 21, 2018 in International (PCT) Application No. PCT/US2017/062825.
Office Action issued Jan. 2, 2020 in U.S. Appl. No. 15/819,986.
Office Action issued Apr. 9, 2020 in U.S. Appl. No. 15/819,986.
Office Action issued Aug. 26, 2020 in U.S. Appl. No. 15/819,986.
Notice of Allowance issued Jan. 13, 2021 in U.S. Appl. No. 15/819,986.

* cited by examiner

BI-LAYER MULTI-WELL CELL CULTURE PLATFORM

RELATED APPLICATIONS

The present application is a continuation of, and claims the benefit of and priority to, U.S. patent application Ser. No. 15/819,986, filed on Nov. 21, 2017, now U.S. Pat. No. 11,001,796, issued on May 11, 2021, which claims the benefit of and priority to, U.S. Provisional Patent Application No. 62/425,658, entitled "BI-LAYER MULTI-WELL CELL CULTURE PLATFORM" and filed on Nov. 23, 206, the entire contents of both of which are hereby incorporated by reference for all purposes.

BACKGROUND

A well plate, also known as a microtiter plate or microwell plate, is a flat plate with multiple wells used as test tubes or petri dishes for cell culturing and other biomedical experiments and analyses. The industry uses a variety of standard sized well plates. For example, 96 well or 384 well plates are standard tools used for research and diagnostic testing.

SUMMARY OF DISCLOSURE

According to one aspect, the disclosure relates to an apparatus that includes a well plate, which includes a plurality of structural layers and a membrane. The membrane separates two structural layers and the well plate defines an array of tissue modeling environments. Each tissue modeling environment includes a first fluid reservoir, a second fluid reservoir, a third fluid reservoir, and a fourth fluid reservoir, with each fluid reservoir configured to hold a column of fluid. Each tissue modeling environment also includes a first microchannel fluidically coupling the first fluid reservoir to the second fluid reservoir, and a second microchannel fluidically coupling the third fluid reservoir to the fourth fluid reservoir, wherein a portion of the first microchannel overlaps at least a portion of the second microchannel across the membrane. In some implementations, the fluid reservoirs of the array or tissue modeling environments are arranged to correspond to the arrangement of wells of a standard 96 well or 384 well plate.

In some implementations, the apparatus further includes a pump assembly. For each tissue modeling environment the pump assembly includes a first output for pumping a first fluid into the first fluid reservoir, a first intake for pumping the first fluid out of the second fluid reservoir, a second output for pumping a second fluid into the third fluid reservoir, and a second intake for pumping the second fluid out of the fourth fluid reservoir. In some implementations, the first intake is coupled to the first output and the second intake is coupled to the second output for each tissue modeling environment. The first or second intake of the pump assembly for at least one tissue modeling environment may be coupled to the first or second output of the pump assembly for a different tissue modeling environment. The pump assembly is configured such that the first fluid flows through the first microchannel with a first flow rate and the second fluid flows through the second microchannel with a second flow rate, different from the first flow rate. In some implementations, the pump assembly is configured to control the first flow rate and the second flow rate for each tissue modeling environment. The pump assembly may also include an actuator. The actuator is configured to induce fluid flow through the pump assembly for a plurality of the tissue modeling environments. The pump assembly may also include at least one separate actuator for independently inducing fluid flow through each respective tissue modeling environment. In some implementations, the actuator is an electromagnetic actuator or a hydraulic actuator.

In some implementations, the plurality of structural layers include a first structural layer, a second structural layer, and a third structural layer, wherein the membrane separates the second structural layer and the third structural layer. The first structural layer includes the fluid reservoirs of the tissue modeling environments. The second structural layer defines the first microchannels of the tissue modeling environments, and the third structural layer defines the second microchannels of the tissue modeling environments in the array of tissue modeling environments.

In some implementations, the plurality of structural layers includes a first structural layer and a second structural layer, wherein the membrane separates the first structural layer and the second structural layer, and the first structural layer defines the fluid reservoirs and the first microchannels of the tissue modeling environments in the array of tissue modeling environments.

In some implementations, the first microchannels or the second microchannels of the tissue modeling environment in the array of tissue modeling environments includes a hydraulic resistor including one or more microchannel restrictors.

In some implementations, one or more cells are attached to a first side or a second side of the membrane in each tissue modeling environment. For example, one or more cells attached to the first side of the membrane may be renal proximal epithelial cells and one or more cells attached to the second side of the membrane may be endothelial cells. In some implementations, the portion of the first microchannel overlapping the second microchannel across the membrane is about 1.0 mm to 30 mm in length, 100 µm to 10 mm in width, and 0.05 mm to 1 mm in depth. In some implementations, the membrane is a track-etched polycarbonate or polyester membrane.

In some implementations, the first microchannel and the second microchannel are defined in an embossed hard plastic. The embossed hard plastic may be a cyclic olefin copolymer (COC), fluorinated ethylene propylene (FEP), polymethylpentene (PMP), polyurethane, polystyrene or polysufone. In some implementations, the first microchannel and the second microchannel are formed from a stack of through-cut layers.

In some implementations, the apparatus further comprises one or more sensor components in each tissue modeling environment. The sensor components may be optical sensors or electrodes.

According to one aspect, the disclosure relates to a method for modeling tissue. The method includes providing a well plate including a plurality of structural layers and a membrane. The membrane separates the two structural layers. The well plate also defines an array of tissue modeling environments. Each tissue modeling environment includes a first fluid reservoir, a second fluid reservoir, a third fluid reservoir and a fourth fluid reservoir, with each fluid reservoir configured to hold a column of fluid. Each tissue modeling environment also includes a first microchannel fluidically coupling the first fluid reservoir to the second fluid reservoir, and a second microchannel fluidically coupling the third fluid reservoir to the fourth fluid reservoir. At least a portion of the first microchannel overlaps at least a portion of the second microchannel across the membrane. The method for modeling tissue modeling environments also includes seeding a first cell type into the first microchannel of each tissue modeling environment, and seeding a second cell type into the second microchannel of each tissue modeling environment. In some implementations, the first cell type may include epithelial cells and the second cell type comprises microvascular cells. The method for modeling tissue modeling environments also includes applying a first feeder flow to the first cell type in the first microchannel of each tissue modeling environment, and applying a second feeder flow to the second cell type in the second microchannel of each tissue modeling environment. In some implementations, the first feeder flow has a first fluid flow rate and the second feeder flow has a second fluid flow rate, different than the first fluid flow rate.

In some implementations, the method for modeling tissue modeling environments also includes introducing a biologically active agent to the array of tissue modeling environments, and measuring the effect of the biologically active agent on the first type of cells or the second type of cells. In some implementations, the biologically active agent also includes introducing different amounts of the biologically active agent into at least two of the tissue modeling environments.

In some implementations, measuring the effect of the biologically active agent on the first or second type of cells includes measuring the effects of the introduction of biologically active agent in different tissue modeling environments having different fluid flow rates.

In some implementations, the method for modeling tissue modeling environments also includes changing a fluid flow rate through the first or the second microchannels of at least one the tissue modeling environment to replicate a hypoxic condition and then measuring the impact of the replicated hypoxic condition on the first or second cell types in at least one tissue modeling environment.

BRIEF DESCRIPTION OF THE DRAWINGS

The foregoing will be apparent from the following more particular description of example implementations of the invention, as illustrated in the accompanying drawings. The drawings are not necessarily to scale, emphasis instead being placed upon illustrating implementations of the present invention.

For purposes of clarity, not every component may be labeled in every figure. The drawings are not intended to be drawn to scale. Like reference numbers and designations in the various figures indicate like elements.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

An industry standard well plate, such as a 96 well plate or a 384 well plate, includes arrays of wells that are used as test tubes or petri dishes. Cells may be deposited into the wells and cultured for further study of microphysiological systems. In microphysiological systems, the rate of change of fluid introduction and withdrawal can have significant effects on media composition and gradients. Providing a constant perfusion of fluid and precisely controlling its flow rate is useful for studying microphysiological systems in a well plate environment. Integrated sensing for real-time direct quantification of culture conditions or tissue response is also useful for studying microphysiological systems in a well plate environment.

The present disclosure describes systems and methods for providing an array of tissue modeling environments with dynamic control of fluid flow. The disclosure describes a cell culture platform with arrays of wells that are fluidically coupled by microchannel structures. A dynamically controlled flow of fluid, when administered through the wells and microchannels, interacts with cells grown within the microchannels. The fluid flow can be used to condition the cells, maintain their growth, perfuse the tissue, supply media/fluids, seed cells, administer mechanical forces/stresses, introduce therapeutic molecules and/or collect samples. The present disclosure also provides systems and methods for providing an array of integrated real time sensors to enable the characterization of tissue conditions and tissue response to exposure to such fluid flows.

In some implementations, systems and methods according to the present disclosure may provide a tissue culture optimization tool in which each tissue modeling environment may be subjected to unique conditions to optimize cell cultures within the tissue modeling environment. In some implementations, systems and methods according to the disclosure may provide a drug screening array in which the tissue in each tissue modeling environment can be screened against a different drug and/or a different dose of the same drug. In some implementations, the systems and methods according to the disclosure can provide drug delivery analysis in which the fluid flow of each tissue unit can be configured to simulate distribution and delivery of a drug in the bloodstream to a tissue. In some implementations, the systems and methods according to the disclosure can provide disease modeling in which each tissue modeling environment or groups of tissue modeling environments can be subjected to unique conditions to model varying disease states.

Figure 1:
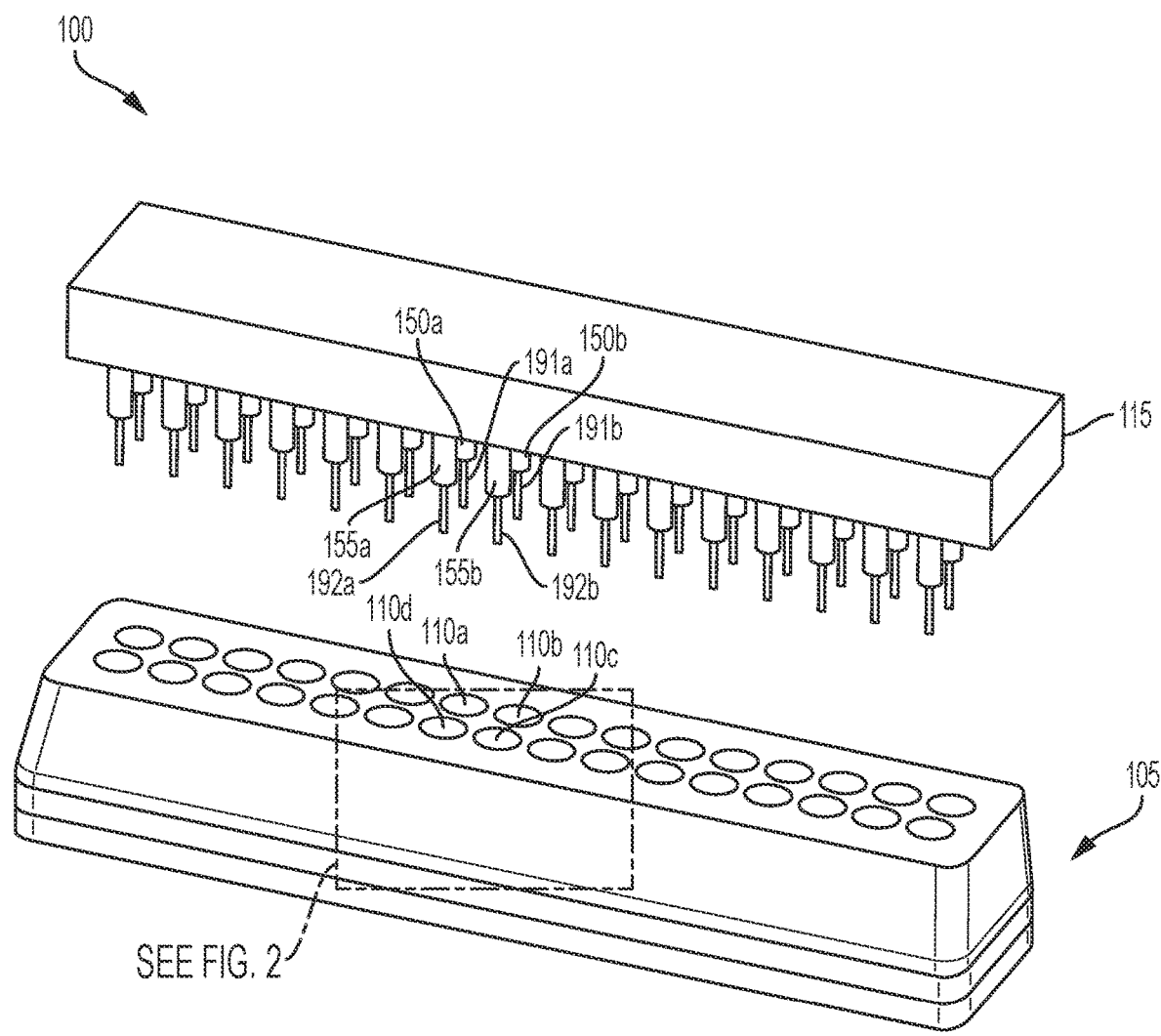
FIG. 1 illustrates an example apparatus for providing an array of tissue modeling environments.

FIG. 1 illustrates an apparatus 100. The apparatus 100 includes a cell culture platform 105 and a pump assembly 115 for providing an array of tissue modeling environments with controlled fluid flow. The cell culture platform 105 includes an array of tissue modeling environments. Each tissue modeling environment includes a group of fluid reservoirs fluidically coupled by a pair of microchannel structures that are separated by a membrane. Each tissue modeling environment includes a group of fluid reservoirs such as a first fluid reservoir 110a, a second fluid reservoir 110b, a third fluid reservoir 110c and a fourth fluid reservoir 110d (generally referred to as fluid reservoirs 110). The fluid reservoirs 110 are each configured to hold a vertical column of fluid. In some implementations, the placement and spacing of the fluid reservoirs 110 of the cell culture platform 105 closely match the placement and spacing of the wells in a standard well plate such as a 96 well or a 384 well plate. This configuration of fluid reservoirs enables the cell culture platform 105 to be compatible with standard industry equipment, such as micropipettes and imaging systems, which are designed for the well configurations of standard well plates.

The pump assembly 115 also includes a plurality of fluid input valves such as a first input valve 150a and a second input valve 150b, as well as a plurality of fluid output valves such as a first fluid output valve 155a and a second fluid output valve 155b. The pump assembly also includes a plurality of input valve sippers such as a first input valve sipper 191a and a second input valve sipper 191b and a plurality of output valve sippers such as a first output valve sipper 192a and a second output valve sipper 192b. When the pump assembly 115 is positioned above the cell culture platform 105, the first and second input valve sippers 191a and 191b and the first and second output valve sippers 192a and 192b are inserted into the columns of fluid in the fluid reservoirs 110. The flow rate through a microchannel fluidically coupling a pair of fluid reservoirs depends partially on the relative fluid heights in the respective fluid reservoirs 110 as maintained by the pumping of fluid from one fluid reservoir to a different fluid reservoir.

The volume of a fluid reservoir may be about 60 μL but may be between about 50 to 115 μL in some implementations. The height of a fluid reservoir may be 11.38 mm but can between about 9 mm to 12 mm to in some implementations. The diameter of the top of a fluid reservoir may be about 3.7 mm but can between about 2.7 mm to 4.7 mm to in some implementations. In some implementations, the fluid reservoir pitch can be about 4.5 mm by 4.5 mm and can have a tolerance of 0.05 in diameter. In some implementations, the fluid reservoirs are tapered towards the bottom to ensure that cells introduced into the fluid reservoirs move through the fluid reservoirs to the membrane 140.

The dimensions of the fluid reservoirs may be altered to achieve a fluid volume to cell count ratio similar to a physiological system to limit any dilution effect. However, in vitro systems can be limited by both the oxygen carrying capacity of the media as well as missing nutrients, hormones, and other secreted factors present in physiological systems. The typical per cell fluid volumes for human physiology may be about 15 pL per cell. A typical 96 well plate may hold about 2000 pL per cell, a typical 24 well plate may hold about 900 pL per cell, and a typical 12 well plate may hold about 6000 pL per cell.

In some implementations, system and methods according to the present disclosure may provide a desirable fluid volume to cell count range of about 100 to 1200 pL per cell, assuming 2,700 cells per $mm^2$.

Figure 2:
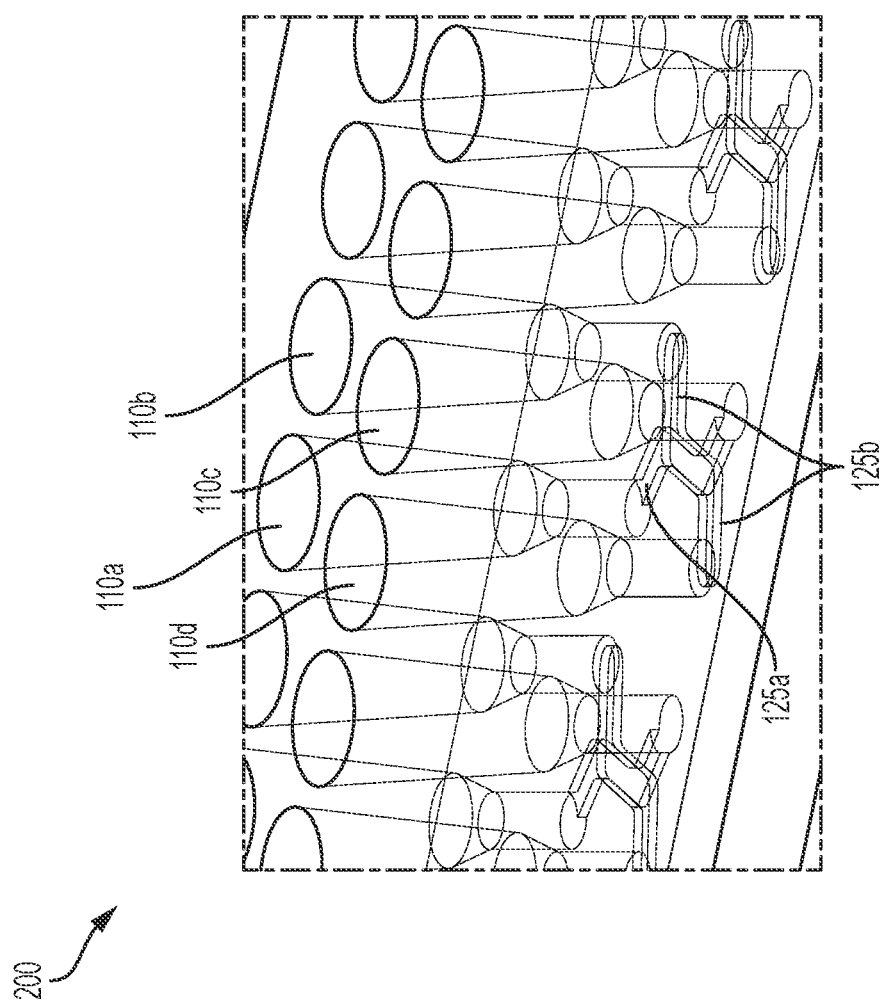
FIG. 2 illustrates a magnified view of a tissue modeling environment provided by the example apparatus illustrated in FIG. 1.

As indicated above, each tissue modeling environment of the cell culture platform 105 also includes a pair of microchannel structures. Each microchannel structure is generally configured to fluidically couple a pair of fluid reservoirs in a tissue modeling environment. FIG. 2 illustrates a magnified view of a tissue modeling environment provided by the example apparatus 100 illustrated in FIG. 1. Each tissue modeling environment of cell culture platform 105 includes a first microchannel 125a and a second microchannel 125b (generally referred to as microchannels 125). The first microchannel 125a fluidically couples the first fluid reservoir 110a to the third fluid reservoir 110c. The second microchannel 125b fluidically couples the second fluid reservoir 110b to the fourth fluid reservoir 110d. A portion of the first microchannel 125a overlaps and runs parallel to at least a portion of the second microchannel 125b.

Figure 3B:
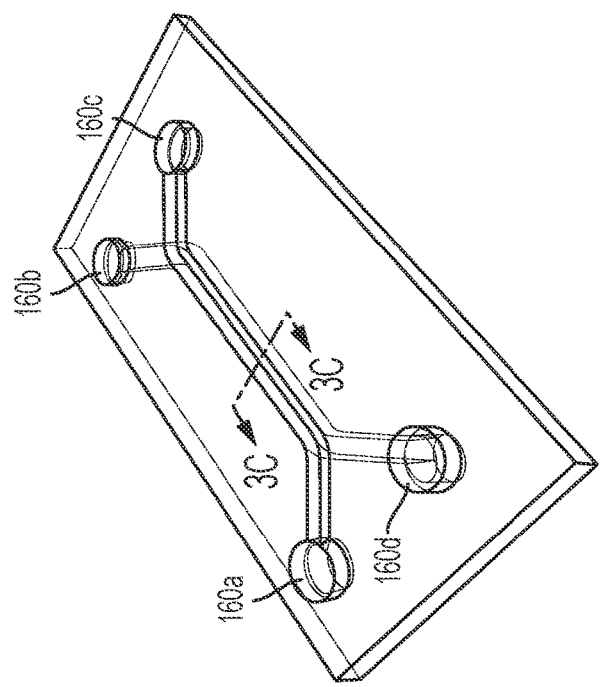
FIG. 3B illustrates a perspective view of the tissue modeling environment illustrated in FIG. 2.
Figure 3C:
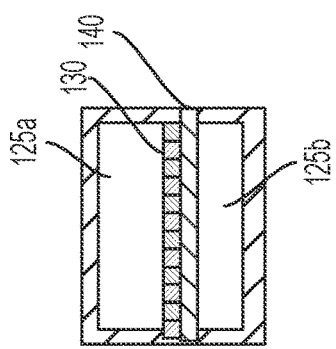
FIG. 3C illustrates a cross sectional view of the tissue modeling environment illustrated in FIG. 2.
Figure 3A:
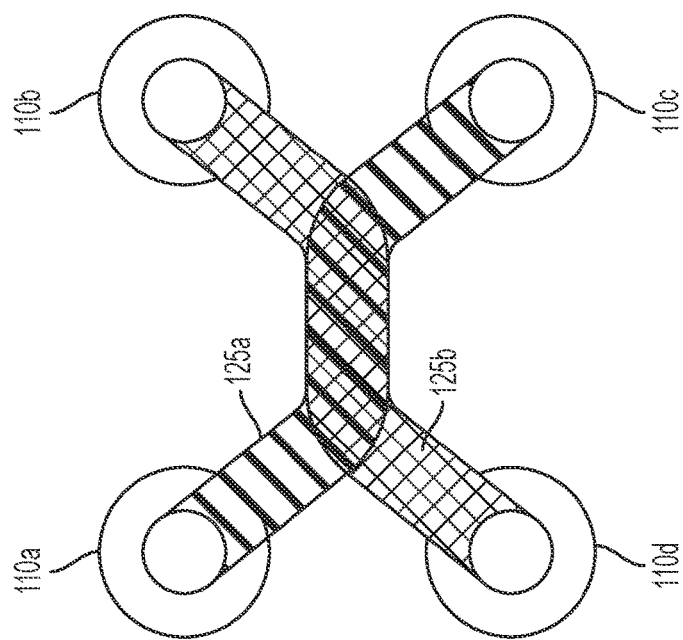
FIG. 3A illustrates a top down view of the tissue modeling environment illustrated in FIG. 2.

FIG. 3A illustrates a top down view of the tissue modeling environment illustrated in FIG. 2. The first microchannel 125a fluidically couples the first fluid reservoir 110a to the third fluid reservoir 110c. The second microchannel 125b fluidically couples the second fluid reservoir 110b to the fourth fluid reservoir 110d. A portion of the first microchannel 125a overlaps and runs parallel to at least a portion of the second microchannel 125b. In some implementations, the microchannels 125 may be fabricated using an embossed hard plastic, thus eliminating disadvantages of microfluidic devices fabricated using soft polymer materials such as PDMS.

FIG. 3B and FIG. 3C illustrates perspective views and cross sectional views, respectively, of the tissue modeling environment illustrated in FIG. 2. In FIG. 3B, the first microchannel 125a is coupled with a first port 160a and a third port 160c, and the second microchannel 125b is coupled with a second port 160b and a forth port 160d (generally referred to as the ports 160). The ports 160 couple the microchannels 125 to the fluid reservoirs 110. As previously indicated, each tissue modeling environment of the cell culture platform 105 also includes a membrane 140. A portion of the first microchannel 125a overlaps and runs parallel to a portion of the second microchannel 125b across the membrane 140. In some implementations, the membrane 140 may have cells 130 attached to it forming living tissue. In some implementations, the membrane 140 may be a semi-permeable membrane with a porosity between about 5 to 90 percent. In some implementations, the membrane 140 may be a semi-permeable track etched membrane with a thickness between about 10 nm to 10 microns. In some implementations the membrane 140 may be a non-permeable membrane. In some implementations, the membrane 140 may be a tensioned membrane. In some implementations, the membrane 140 may be a non-tensioned membrane that includes fluorinated ethylene propylene (FEP). In some implementations, the membrane 140 may include a scaffolding of polycarbonate, polyethylene terephthalate (PET) or polyamide. In some implementations, the membrane 140 may include a hydrogel, gel or cross linked elastomer.

In some implementations, cells of the same cell type or cells of different cell types may be attached to each side of the membrane 140 or the walls of the microchannels to create a co-culture. In some implementations, renal proximal epithelial tissue may be seeded on the apical or top surface of the membrane 140 while endothelial cells may be seeded on the bottom surface of the membrane 140 to approximate the in vivo structure of the renal tubule. In some implementations, intestinal epithelial cells may be seeded on the top surface of the membrane 140 and endothelial cells may be seeded on the bottom surface of the membrane 140 to approximate the in vivo structure of gastrointestinal tissue. In some implementations, airway epithelial cells may be seeded on the top surface of the membrane 140 and endothelial cells may be seeded on the bottom surface of the membrane 140 to approximate the in vivo structure of airway tissue, lung tissue, or tracheobronchial tissue. In some implementations, tumor cells may be seeded on the top surface of the membrane 140 and endothelia cells may be seeded on the bottom surface of the membrane 140 to approximate the in vivo structure of a tumor environment. In some implementations, hepatocyte cells may be seeded on the top surface of the membrane 140 and endothelial cells may be seeded on the bottom surface of the membrane 140 to approximate the in vivo structure of a liver sinusoid. In some implementations, hepatocyte cells may be seeded on the top surface of the membrane 140 and stellate cells and Kupffer cells may be seeded on the bottom surface of the membrane 140 to approximate the in vivo structure of liver tissue. In some implementations, pericytes or smooth muscle cells may be seeded on the top surface of membrane 140 and endothelial cells may be seeded on the bottom surface of the membrane 140 to approximate the in vivo structure of vascular tissue. In some implementations, oral keratinocytes or fibroblasts may be seeded on the top surface of the membrane 140 and endothelial cells may be seeded on the bottom surface of the membrane 140 to approximate the in vivo structure of oral tissue, for example, gum tissue. In some implementations, epidermal keratinocytes or fibroblasts may be seeded on the top surface of the membrane 140 and endothelial cells may be seeded on the bottom surface of the membrane 140 to approximate the in vivo structure of skin tissue. In some implementations, central nervous system cells may be seeded on the top surface of the membrane 140 and endothelial cells may be seeded on the bottom surface of the membrane 140 to approximate the in vivo structure of a blood brain barrier tissue. In some implementations, syncytiotrophoblasts may be seeded on the top surface of membrane 140 and endothelial cells may be seeded on the bottom surface of membrane 140 to approximate the in vivo structure of placental barrier tissue. In some implementations, immune cells, such as T cells, may be included in any cell combination to approximate an in vivo tissue response to an immune interaction component.

In some implementations, one or more portions of a tissue modeling environment may include a cell-phobic coating to selectively prevent cells introduced into the tissue modeling environment from adhering to the coated areas. In some implementations, portions of a tissue modeling environment may include a cell-binding coating to selectively bind cells introduced into the tissue modeling environment to the coated portions. In some implementations, the cell-binding coating may be used in place of or in conjunction with the cell-phobic coating. In some implementations, the cell-phobic coating and the cell-binding coating may include patterns, cell adhesion molecules (CAMs) or nanotopographic patterns. In some implementations, at least one surface of the membrane 140 includes a topographical pattern. In some implementations, the topographical pattern may be a nanotopographical pattern. In some implementations, the topographical pattern on at least a portion of at least one surface of the membrane 140 is selected to promote increased adhesion of cells to at least one surface of the membrane 140, as described in U.S. application Ser. No. 13/525,085, the entirety of which is incorporated herein by reference. For example, in some implementations, the design of the topographic surface allows close control of cells grown atop the substrate. In some implementations, the topographic surface, along with additional flow channel parameters such as channel height, channel cross-sectional area, and flow rate, can be used to create highly controlled in vitro conditions that closely mimic the in vivo environment of specific cells types. For example, in some implementations, a pattern of grooves and ridges, like an extracellular matrix, may causes kidney cells to lengthen and align themselves parallel to the ridges, encourage cell-to-cell junctions, and promote the adhesion of the cells to the surface. In some implementations, the membrane surface can have grooves and ridges that are narrower than the cells. In some implementations, the grooves and ridges are approximately the same width, although they do not have to be.

As shown in FIGS. 2 and 3A-3C a portion of the first microchannel 125a overlaps and runs in parallel to at least a portion of the second microchannel 125b. In some implementations, one or more portions of the first microchannel 125a and the second microchannel 125b may overlap one or more portions of the second microchannel 125b without the channels running parallel to one another at the overlap. For example, in some implementations, at least one of the first microchannel 125a and the second microchannel 125b may have a serpentine shape and may cross each other at various points.

In some implementations, the microchannels 125 may be between about 1 to 30 mm in length. In some implementations, the microchannels 125 may be between about 100 to 10 mm in width. In some implementations, the microchannels 125 may be between about 0.05 mm to 1 mm in depth. FIGS. 9A-9F below further illustrate example implementations of the microchannels 125.

FIGS. 9A-9F show example implementations of the microchannels 125. FIGS. 9A-9F represent a variety of channel configurations that can be built into the platform 105. Each structure accomplishes one or more design goals that enhance the functionality of the well plate platform for a variety of corresponding use cases depending on the geometrical and biophysical requirements of particular tissue models being cultured. The solid lines in the Figures represent the first microchannel 125a and dashed lines represent second microchannel 125b. As previously mentioned, the first microchannel 125a fluidically couples the first reservoir 110a to the third reservoir 110c. The second microchannel 125b fluidically couples the second reservoir 110b to the fourth reservoir 110d. Each of each microchannel has a port 160 connecting the microchannel 125 to a corresponding fluid reservoir 110.

Figure 9A:
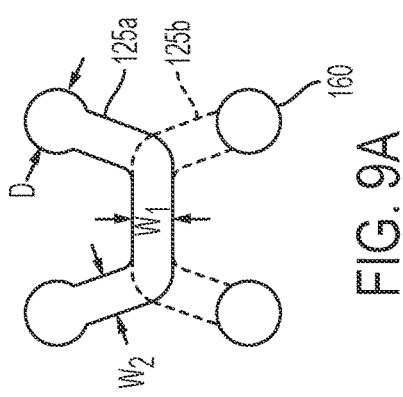
FIGS. 9A-9F illustrates top down views of various example implementations of microchannel structures.

FIG. 9A illustrates a top down view of an example implementation of microchannels 125 in a cis orientation. In a cis orientation, the ports 160 for each microchannel are on the same side of the channel. In FIG. 9A, the width $W_1$ of the overlapping portions of the microchannels may be about 1.0 to 1.5 mm and the width $W_2$ of the non-overlapping portions of the microchannels may be about 0.75 to 1.0 mm. In some implementations, the depth (not shown) of the microchannels may be about 100 to 200 In some implementations, the depth (not shown) of the microchannels may be about 100 to 300 In some implementations, the diameter D of the ports 160 may be about 100 to 300 In some implementations, the diameter D of the ports 160 may be about 500 to 1500 The length of the overlapping portions of the microchannels channels may be between 6 to 8 mm, for example 7 mm.

Figure 9B:
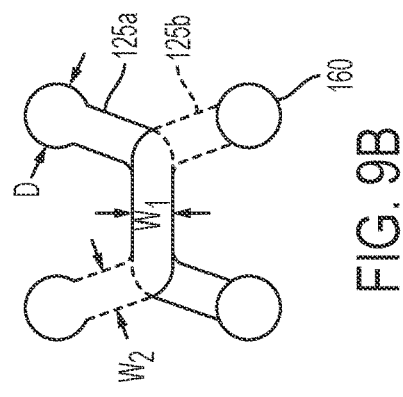

FIG. 9B illustrates a top down view of an example implementation of microchannels 125 in a trans orientation. In a trans orientation, the ports 160 for each microchannel are on opposite sides of the channel. In FIG. 9B, the width $W_1$ of the overlapping portions of the microchannels may be about 1.0 to 1.5 mm and the width $W_2$ of the non-overlapping portions of the microchannels may be about 0.75 to 1.0 mm. In some implementations, the depth (not shown) of the microchannels may be about 100 to 200 In some implementations, the depth (not shown) of the microchannels may be about 100 to 300 In some implementations, the diameter D of the ports 160 may be about 100 to 300 In some implementations, the diameter D of the ports 160 may be about 500 to 1500 The length of the overlapping portions of the microchannels channels may be between 6-8 mm, for example 7 mm.

Figure 9C:
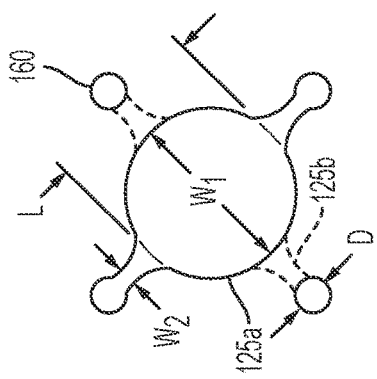

FIG. 9C illustrates a top down view of an example implementation of microchannels 125. The implementation of FIG. 9C maximizes the overlapping area of the microchannels 125, where the overlap area may be between 80% to 85% of total microchannel area, for example 82%. The width $W_1$ of the overlapping portions of the microchannels may be about 3 to 4.25 mm. The width $W_2$ of the non-overlapping portions of the microchannels may about 0.5 to 1 mm. The length of the microchannel L may be about 3.0 to 4.25 mm. The depth (not shown) may be about 100 to 300 The diameter D of the ports 160 may be about 0.5 to 1.5 mm.

Figure 9D:
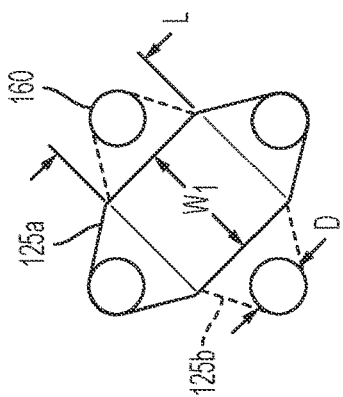

FIG. 9D illustrates a top down view of an example implementation of microchannels 125. FIG. 9D maximizes cell culture area of the microchannels 125, where the cell culture area may be between 20 mm$^2$ and 30 mm$^2$, for example 25.4 mm$^2$. The width $W_1$ of the overlapping portions may be about 3.0 to 4.25 mm. The length L may be about 3 to 4.25 mm and the depth (not shown) may be about 100 to 300 The diameter D of the ports 160 may be about 0.75 to 1.5 mm.

Figure 9E:
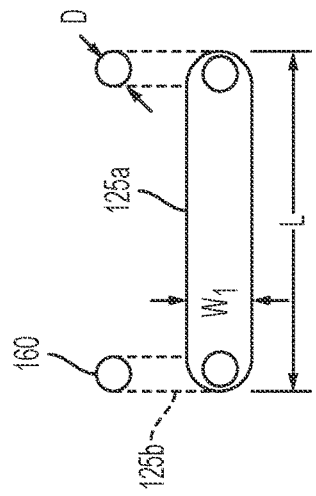

FIG. 9E illustrates a top down view of an example implementation of microchannels 125. The implementation of FIG. 9E creates a uniform flow field in both upper and lower microchannels 125. The width $W_1$ of the overlapping portions of the microchannels may be about 1.0 to 3.5 mm. The width $W_2$ of the non-overlapping portions of the microchannels may be 0.5 to 1.5 mm. In some implementations, the depth (not shown) of the microchannels may be about 100 to 250 In some implementations, the depth (not shown) of the microchannels may be about 100 to 300 μm. The diameter D of the ports 160 may be about 1.0 to 1.5 mm. FIG. 9E may be orientated in a linear orientation formed from four ports 160 arranged in a single row or column of a well plate instead of a 2×2 grouping of wells.

Figure 9F:
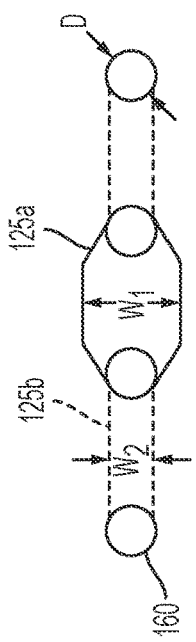

FIG. 9F illustrates a top down view of an example implementation of microchannels 125. FIG. 9F creates a high overlap area of about 70% to 80%. In some implementations, the overlap area may be about 76%. The upper channel has a uniform flow field because the ports are linearly connected to the microchannel 125a, compared to microchannel 125b where the ports are located at an angle to microchannel 125b. The width $W_1$ of the microchannel overlap may be about 3.0 to 4.25 mm. The length L may be about 6.0 to 7.5 mm. The depth (not shown) may be about 100 to 300 The port diameter D may be about 0.5 to 1.5 mm.

In some implementations, the fluid flow through the microchannels 125 may be used to condition the cells attached to the membrane 140, maintain their growth, perfuse the tissue, supply media/fluids, seed cells, introduce therapeutic molecules and collect samples. In some implementations, fluid pumped through the microchannels 125 may include suspended cells, for example blood cells. In some implementations, the flow rates and media composition through a tissue modeling environment may be different in each of the microchannels 125 while interacting through the tissue attached to the membrane 140. In some implementations, the flow rate through the first microchannel 125a or the second microchannel 125b or both microchannels 125a and 125b may be zero.

The difference in fluid column height between a pair of fluid reservoirs causes a gravity fed fluid flow through the first and second microchannels 125a and 125b. A fluid flow through both the first microchannel 125a and the second microchannel 125b maintains a pressure gradient across the membrane 140 within the microchannels 125. In some implementations, the fluid flows through the microchannels 125 may be used to administer mechanical forces and stresses across the membrane 140. The shear rate applied to the membrane 140 within the microchannels 125 is determined by the flow rate through the microchannels 125 and their dimensions as well as the geometry of the overlapping portion of the first microchannels 125a and the second microchannel 125b. In some implementations, a hydraulic resistance in the microchannels 125 may be fixed or varied through the use of channel restrictors that are actuated. The advantage of having variable hydraulic resistance in the microchannels 125 is that the shear stress applied to the membrane 140 within the microchannels 125 may be varied in a customized, "plug and play" manner in contrast to a cell culture platform with fixed microchannel dimensions. In some implementations, additional time-varying controls through the actuation of pumps and valves or by manipulation of distensible walls of the microchannels 125 can be used to introduce pulsatile or time-varying shear rates upon cultured cell populations within the microchannels 125. In some implementations, the cell culture platform 105 and/or pump assembly 115 may include hydraulic capacitive or compliant elements.

When a pair of fluid reservoirs are fluidically coupled by a microchannel, a difference in height between a column of fluid in each fluid reservoir causes a gravity fed fluid flow through the microchannel. Controlling the difference in fluid column height between a pair of fluid reservoirs controls the rate of the fluid flow through a microchannel. A difference in height between the columns of fluid in a pair of fluid reservoirs is achieved by introducing fluid into one fluid reservoir and/or removing fluid from another fluid reservoir through a pathway other than the microchannel. A desired fluid flow rate through a microchannel is produced by maintaining an approximately constant difference in fluid column height between the pair of fluid reservoirs by introducing and removing fluid from their fluid columns at a rate that is equal to the desired fluid flow rate. A controlled fluid flow, when administered through the fluid reservoirs and the microchannel structures of a tissue modeling environment, interacts with cells attached to the membrane within the microchannel structures.

Flow rates can be determined from a number of different biological requirements including transport, reaction kinetics, and mechanical effects (e.g. shear). Transport can be calculated from the convective diffusion equation, known to persons of ordinary skill in the art. In the case where transport is an important biological design principle, e.g. hepatocytes, matching the in vitro model transport regime to the physiological transport regime can be accomplished using the Peclet number, a dimensionless parameter that indicates the ratio of convective to diffusive transport, where Pe=UL/D; wherein L is the length, U is the velocity magnitude, and D is a characteristic diffusion coefficient. The channel geometry will set the length, L, the diffusing species and media will determine the diffusion coefficient, D, and the flow rate can then be determined from the channel geometry and the mean velocity, U. For transport without reaction, the Peclet number is an appropriate scaling parameter. For example, in vivo estimates of the Peclet number in the blood compartment of the liver sinusoid are between 2 and 10.

Fluid flow within microchannels 125 creates shear stress on the membrane 140. Shear stress can be calculated by solving the Naiver Stokes equation of fluid flow, but has been reduced to analytical solutions known to persons of ordinary skill in the art for simplified geometries. For the cases where flow pulsatility is an important parameter, estimates can be made using the system capacitance and resistance. For a pressure driven flow from an open reservoir of constant cross-section, the capacitance and resistance are given respectively by:

$$C = \frac{\text{Well Surface Area}}{\rho g};$$

wherein C is the fluidic capacitance, $\rho$ is the fluidic density, and g is the gravity constant $$9.81 \frac{m}{s^2},$$

and $$R = \frac{\Delta P}{Q};$$

where R is the system fluidic resistance, $\Delta P$ is the pressure difference and Q is the flow rate. The fluidic time constant is given by the product of the fluidic capacitance, C, and the fluidic resistance, R. To minimize flow pulsatility, the system may be designed such that the pump cycle is significantly less than the fluidic time constant. The change in flow rate between cycles may be estimated by:

$$Q = Q_O e^{-t/RC}$$

where t is time and $Q_O$ is the flow rate at t=0.

These equations together with the system constraints, including biological constraints, fabrication, materials, etc., can be combined to create a solution envelope of possible geometrics satisfying all constraints.

As previously indicated, the example apparatus 100 in FIG. 1 also includes a pump assembly 115. The pump assembly 115 is generally configured to provide controlled fluid flow to each tissue modeling environment of the cell culture platform 105 by pumping fluid into and out of the tissue modeling environment through a plurality of fluid input valves and fluid output valves. The pump assembly 115 includes a plurality of fluid input valves such as a first fluid input valve 150a and a second fluid input valve 150b (generally referred to as the fluid input valves 150). The pump assembly 115 also includes a plurality of fluid output valves such as a first fluid output valve 155a and a second fluid output valve 155b (generally referred to as the fluid output valves 155). The fluid input valves and the fluid output valves are check valves. The fluid input valves are generally configured to intake fluid flow into the pump assembly 115 while the fluid output valves are generally configured to output fluid flow out of the pump assembly 115.

The pump assembly 115 includes a plurality of input valve sippers and a plurality of output valve sippers. The input valve sippers and the output valve sippers are generally configured to enable the fluid input valves 150 and the fluid output valves 155 to be in fluid communication with the fluid reservoirs 110. A first fluid input valve 150a is coupled to a first input valve sipper 191a, a second fluid input valve 150b is coupled to a second input valve sipper 191b, a first fluid output valve 155a is coupled to a first output valve sipper 192a and a second fluid input valve 155b is coupled to a second output valve sipper 192b. When the pump assembly 115 is positioned above the cell culture platform 105, the first and second input valve sippers 191a and 191b and the first and second output valve sippers 192a and 192b are inserted into the columns of fluid in the fluid reservoirs 110 at different depths. The flow rate through a microchannel fluidically coupling a pair of fluid reservoirs depends partially on the depth of the input valve sippers and the output valve sippers in the fluid reservoirs 110.

When the pump assembly 115 is positioned above the cell culture platform 105, the fluid input valves 150 and the fluid output valves 155 of the pump assembly 115 are in fluid communication with the fluid reservoirs 110. The first fluid input valve 150a and the first input valve sipper 191a and the second fluid input valve 150b and the second input value sipper 191b are each in fluid communication with a column of fluid in the first fluid reservoir 110a and the second fluid reservoir 110b, respectively. The first fluid output valve 155a and the first output value sipper 192a and the second fluid output valve 155b and the second output value sipper 192b are each in fluid communication with a column of fluid in the fourth fluid reservoir 110d and the third fluid reservoir 110c, respectively. The pump assembly 115 pumps a fluid out of the first fluid reservoir 110a through the first fluid input valve 150a and the first input valve sipper 191a. The pump assembly 115 pumps a fluid out of the second fluid reservoir 110b through the second fluid input valve 150b and the second input valve sipper 192b. The pump assembly 115 pumps fluid into the forth fluid reservoir 110d through the first output value 155b and the first output value sipper 192a. The pump assembly pumps fluid into the third fluid reservoir 110c through the second fluid output valve 155b and the second output valve sipper 192b.

Figure 4B:
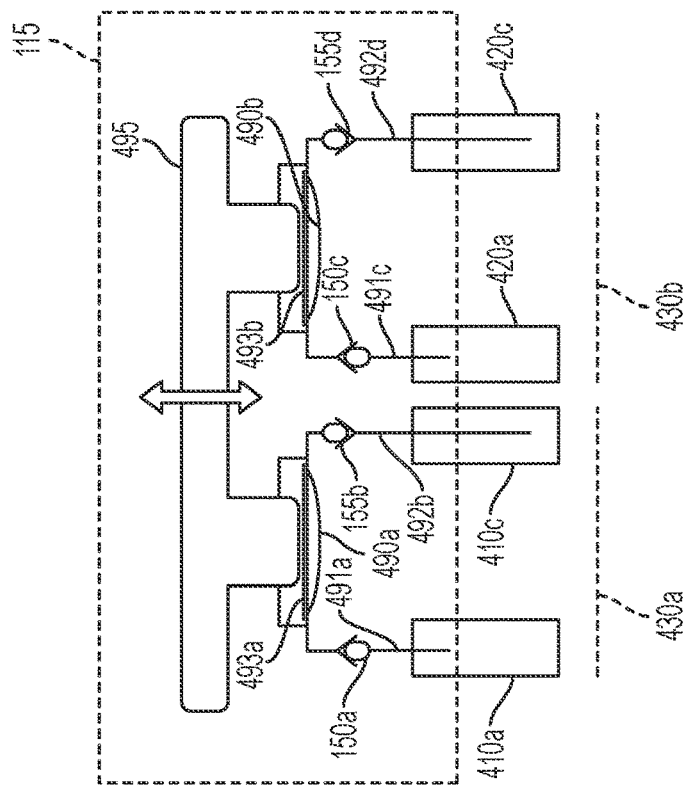
FIG. 4B illustrates the pump assembly interacting with the first and second tissue modeling environments shown in FIG. 4A.
Figure 4A:
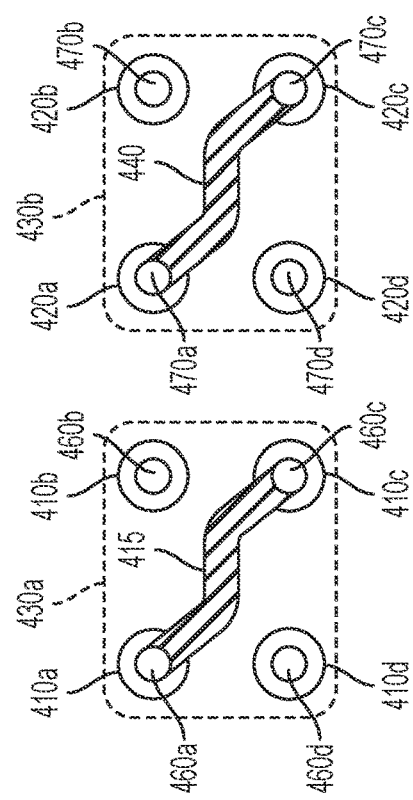
FIG. 4A illustrates a top down view of two adjacent tissue modeling environments of the cell culture platform 105 in FIG. 1.

FIG. 4A illustrates a top down view of two adjacent tissue modeling environments 430a and 430b (each generally referred to as a tissue modeling environment 430) of the cell culture platform 105 in FIG. 1. Each of the tissue modeling environments 430 includes a plurality of fluid reservoirs. The first tissue modeling environment 430a includes a first fluid reservoir 410a, a second fluid reservoir 410b, a third fluid reservoir 410c and a fourth fluid reservoir 410d. The first fluid reservoir 410a and the third fluid reservoir 410c are fluidically coupled by a first microchannel 415. While not shown in FIG. 4A, the second fluid reservoir 410b and the fourth fluid reservoir 410d are also fluidically coupled by a microchannel. The first tissue modeling environment 430a also includes a plurality of ports. The first tissue modeling environment includes a first port 460a, a second port 460b, a third port 460c, and a forth port 460d. The first port 460a couples the first microchannel 415 to the first fluid reservoir 410a. The second port 460b couples the second microchannel to the second fluid reservoir 410b. The third port 460c couples the first microchannel 415 to the third fluid reservoir 410c, and the forth port 460d couples the second microchannel to the forth fluid reservoir 410d. The second tissue modeling environment 430b includes a first fluid reservoir 420a, a second fluid reservoir 420b, a third fluid reservoir 420c and a fourth fluid reservoir 420d. The first fluid reservoir 420a and the third fluid reservoir 420c are fluidically coupled by a first microchannel 440. While not shown in FIG. 4A, the second fluid reservoir 420b and the fourth fluid reservoir 420d are also fluidically coupled by a microchannel. The second tissue modeling environment 430b also includes a plurality of ports. The second tissue modeling environment 430b includes a first port 470a, a second port 470b, a third port 470c, and a forth port 470d. The first port 470a couples the first microchannel 440 to the first fluid reservoir 420a. The second port 470b couples the second microchannel to the second fluid reservoir 420b. The third port 470c couples the first microchannel 440 to the third fluid reservoir 420c, and the forth port 470d couples the second microchannel to the forth fluid reservoir 420d.

FIG. 4B illustrates the pump assembly 115 interacting with the first and second tissue modeling environments 430a and 430b shown in FIG. 4A. The first fluid input valve 150a is coupled to a first input sipper 491a and is in fluid communication with a column of fluid in the first fluid reservoir 410a of the first tissue modeling environment 430a. The second fluid input valve 150b (not shown in FIG. 4A or FIG. 4B) of the pump assembly 115 is adjacent to the first fluid input valve 150a. A third fluid input valve 150c is coupled to a third input sipper 491c and in fluid communication with a column of fluid in the first fluid reservoir 420a in the second tissue modeling environment 430b. A fourth fluid input valve 150d (not shown in FIG. 4A or FIG. 4B) of the pump assembly 115 is adjacent to the third fluid input valve 150c.

The pump assembly 115 includes a first fluid output valve 155a (not shown in FIG. 4A or FIG. 4B). The second fluid output valve 155b is coupled to a second output sipper 492b and is in fluid communication with a column of fluid in the third fluid reservoir 410c of the first tissue modeling environment 430a. A third fluid output valve 155c (not shown in FIG. 4A or FIG. 4B) of the pump assembly 115 is adjacent to the second fluid output valve 155b. A fourth fluid output valve 155d is coupled to a fourth output sipper 492a and is in fluid communication with a column of fluid in the third fluid reservoir 420c in the second tissue modeling environment 430b.

The pump assembly 115 further includes an actuator 495. The actuator 495 is generally configured to control a fluid flow through the first tissue modeling environment 430a and a fluid flow the second tissue modeling environment 430b. The actuator 495 pumps fluid flow through the first input valve 150a and the second output valve 155b in the first tissue modeling environment 430a and the third input valve 150c and the fourth output valve 155d in the second tissue modeling environment 430b. The pump assembly further includes a first pump chamber 490a, a second pump chamber 490b (generally referred to as the pump chambers 490), a first pump chamber diaphragm 493a and a second pump chamber diaphragm 493b (generally referred to as the pump chamber diaphragms 493). The pump chamber diaphragms 493 are tensioned. The first pump chamber 490a and the second pump chamber 490b are each generally configured to hold a fluid.

The pump assembly 115 pumps a fluid into the third fluid reservoir 410c and 420c of the first and second tissue modeling environments 430a and 430b. As previously indicated, the pump chamber diaphragms 493 are tensioned and can be depressed by the actuator 495. When the actuator 495 is lowered, it depresses the pump chamber diaphragms 493 into the pump chambers 490 causing fluid in the pump chambers 490 to flow through the second fluid output valve 155b and the fourth fluid output valve 155d (generally referred to as the fluid output valves 155) and into the third fluid reservoirs 410c and 420c of the first and second tissue modeling environments 430a and 430b. As the fluid flows into the third fluid reservoirs 410c and 420c of the first and second tissue modeling environments 430a and 430b produces a difference in fluid column height between the first fluid reservoirs 410a and 420a and the third fluid reservoirs 410c and 420c causing a gravity fed fluid flow through the microchannels 415 and 440.

The pump assembly 115 pumps a fluid out of the first fluid reservoirs 410a and 420a of the first and second tissue modeling environments 430a and 430b. When the actuator 495 retracts from the pump chamber diaphragms 493, the tensioned pump chamber diaphragms 493 return to their rest position, pulling a vacuum on the pump chambers 490, and causing fluid to move out the first fluid reservoirs 410a and 420a of the first and second tissue modeling environments 430a and 430b through the first fluid input valve 150a and the third fluid input valve 150c (generally referred to as the fluid input valves 150) and into the pump chambers 490. As the fluid flows out of the first fluid reservoirs 410a and 420a of the first and second tissue modeling environments 430a and 430b, gravity fed flow causes the fluid column heights of the first fluid reservoirs 410a and 420a and the third fluid reservoirs 410c and 420c to equalize.

In some implementations, a separate actuator may be provided for each tissue modeling environment and may be independently controlled for each tissue modeling environment. In some implementations, the actuators provided for the tissue modeling environments may be independently controlled with electromagnetic actuators. In other implementations, a single actuator may drive fluid flow for multiple tissue modeling environments within a cell culture platform. In other implementations, a single actuator may drive fluid flow for all of the tissue modeling environments within a cell culture platform. In some implementations, the fluid input and output valves may be duckbill style valves, valves composed of asymmetric diffusers or other directionally-biased flow valves. Other implementations may include actuator and fluid valve configurations described in U.S. application Ser. No. 15/016,227, the entirety of which is incorporated by reference.

In some implementations, the pump assembly 115 is controlled by a controller. In some implementations, the controller outputs actuation and control signals to the actuator for each tissue modeling environment in the array of tissue modeling environments. In some implementations, the controller may include a user interface, by which the user may enter in the desired flow rates for each tissue modeling environment. In some implementations, the controller is further configured to receive, store, and process, sensor data collected by the sensors discussed further below. The results of the sensor data processing can be outputted via the user interface. In some implementations, the controller includes software executing on a general purpose processor configured to provide the above-referenced user interface and to output the above-mentioned control signals.

In some implementations, the pump chamber diaphragms may be non-tensioned and thus are unable to return to a rest position upon retraction of the reservoir. The pump chamber diaphragms in such implementations must be actively pulled back to their non-depressed position. Such pumps can be driven, in some implementations, by pneumatic fluid flow, where introduction of a fluid distends the diaphragm into the pump chamber cavity, and withdrawal of the pneumatic fluid creates a vacuum which actively retracts the diaphragm.

Figure 10:
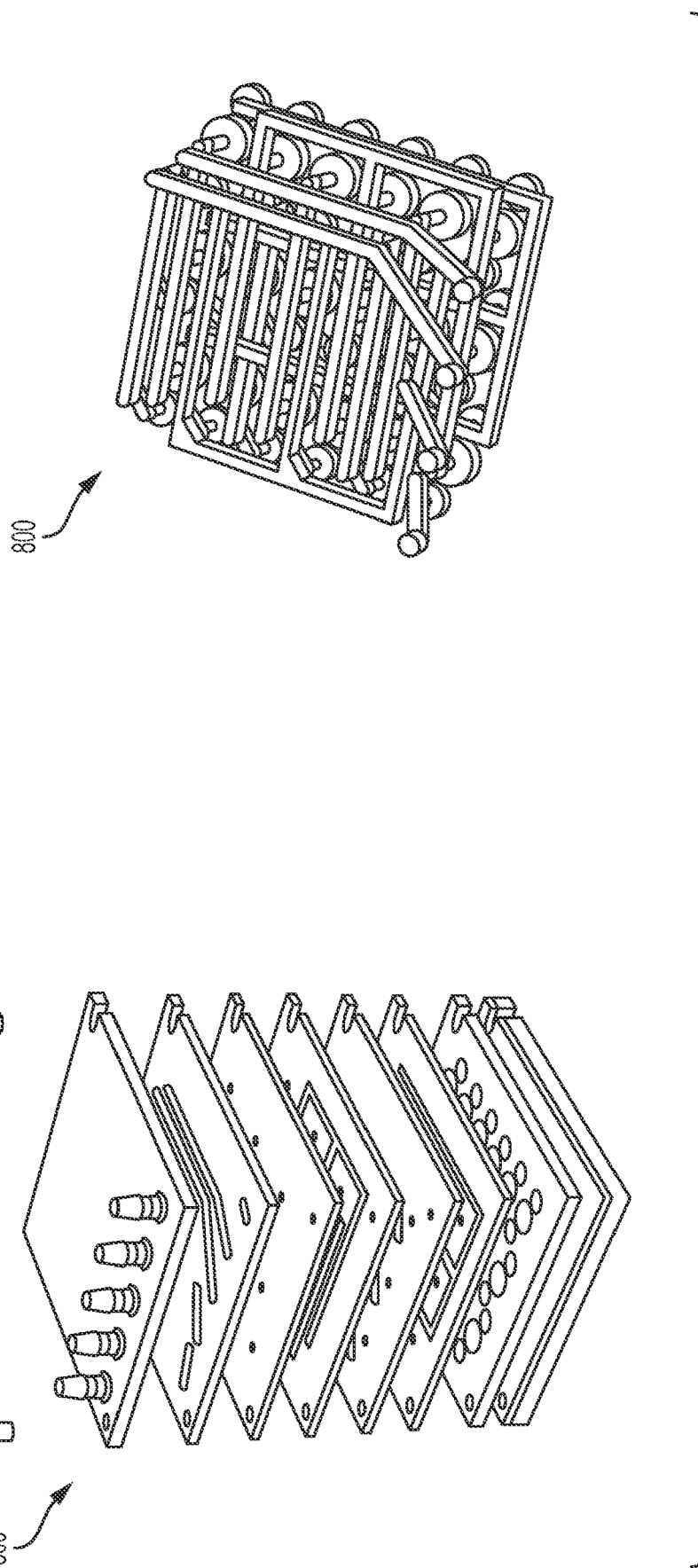
FIG. 10 illustrates views of an example pneumatic manifold actuator and pump assembly.
Figure 11:
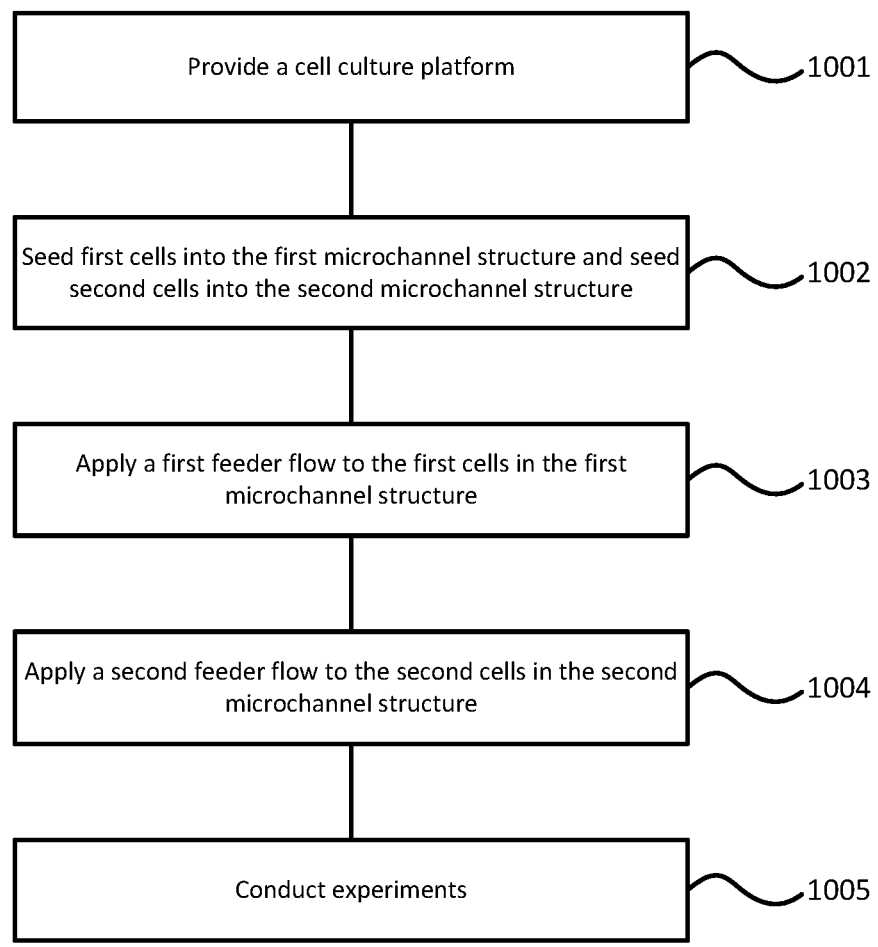
FIG. 11 illustrates a flow chart of an example method for populating cells into the cell culture platform of FIG. 1.
Figure 12:
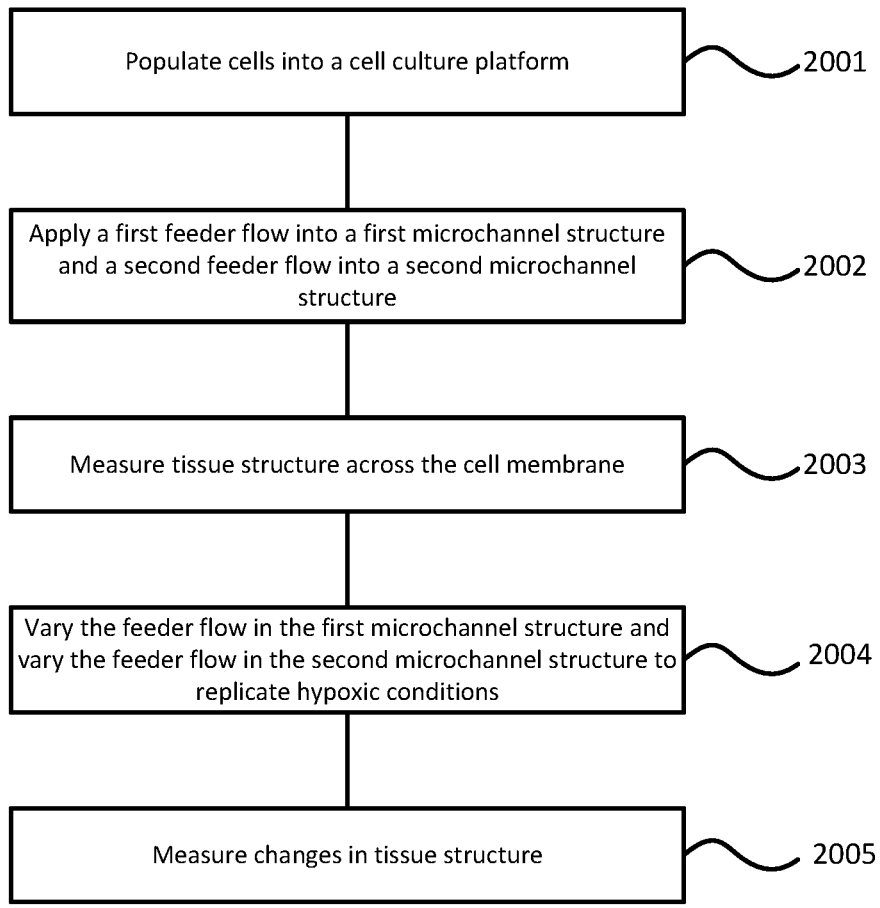
FIG. 12 illustrates a flow chart of an example experimental method for simulating hypoxic conditions in healthy tissue using the cell culture platform of FIG. 1.

FIG. 10 illustrates two views of an example pneumatic pump assembly 800 suitable for driving pumps with non-tensioned or tensioned membranes. The pneumatic pump assembly 800 includes pneumatic pump lines that provide pneumatic fluid to and from rows of pumps in the pump assembly 800 such that the pumps in those rows act in unison. For example, one row of pumps may control the flow of fluid that passes through the first microchannels 125a of multiple cell culture environments, while another row of pumps may control the flow of fluid that passes through the second microchannels 125b of those cell culture environments. The pump assembly 800 can also include fluid lines for applying bias pressures to passive valves included in the pump assembly 800.

Figure 5A:
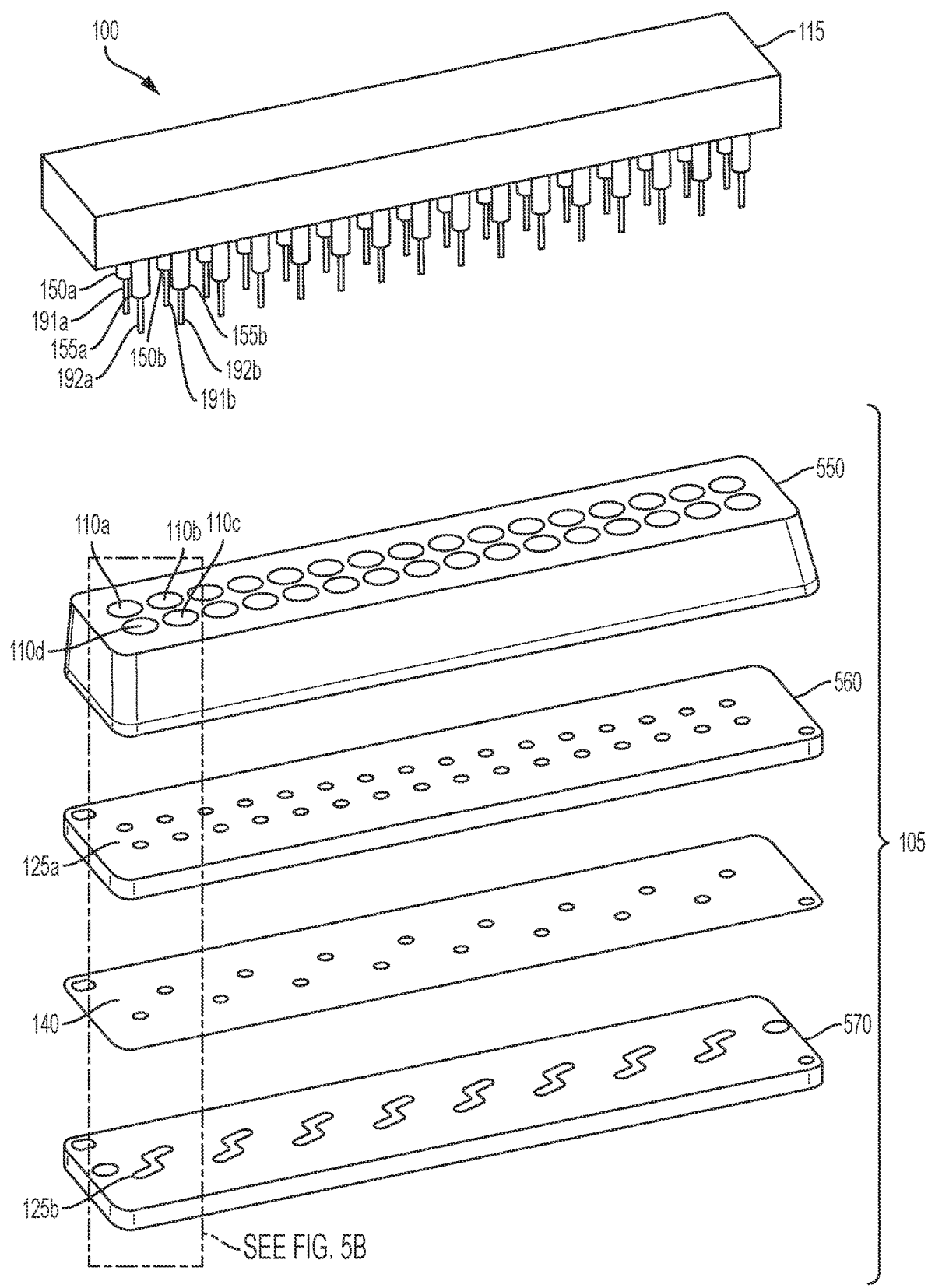
FIG. 5A illustrates an exploded view of the cell culture platform of the example apparatus illustrated in FIG. 1.

FIG. 5A illustrates an exploded view of the cell culture platform 105 of the example apparatus 100 illustrated in FIG. 1. An array of tissue modeling environments in a cell culture platform is defined by structural layers separated by a membrane. The cell culture platform 105 includes a first structural layer 550 that further includes a plurality of fluid reservoirs 110, a second structural layer 560 and a third structural layer 570 separated by a membrane 140. The fluid reservoirs 110 are each configured to hold a vertical column of fluid. The underside of the second structural layer 560 defines a first set of microchannel structures (shown in FIG. 5B), such as first microchannels 125a. The first microchannels 125a fluidically couple the first fluid reservoirs 110a to the third fluid reservoirs 110c. The third structural layer 570 defines a second set of microchannel structures, such as the second microchannels 125b. The second microchannels 125b fluidically couple the second fluid reservoirs 110b to the fourth fluid reservoirs 110d. A membrane 140 separates the first set of microchannels defined by the second structural layer 560, such as the first microchannel 125a and the second set of microchannels defined by the third structural layer 570 such as the second microchannel 125b. When the first structural layer 550, the second structural layer 560 and the third structural layer 570 are stacked, portions of the first microchannels 125a overlap and run parallel to portions of the second microchannels 125b across the membrane 140. In some implementations, at least one of the first microchannels 125a and the second microchannels 125b may have a serpentine shape and may cross each other at various points. In some implementations, the microchannels 125 may be between about 1 to 30 mm in length. In some implementations, the microchannels 125 may be between about 100 μm to 10 mm in width. In some implementations, the microchannels 125 may be between about 0.05 mm to 1 mm in depth. FIGS. 9A-9F, discussed above, further illustrate example implementations of the microchannels 125.

Figure 5B:
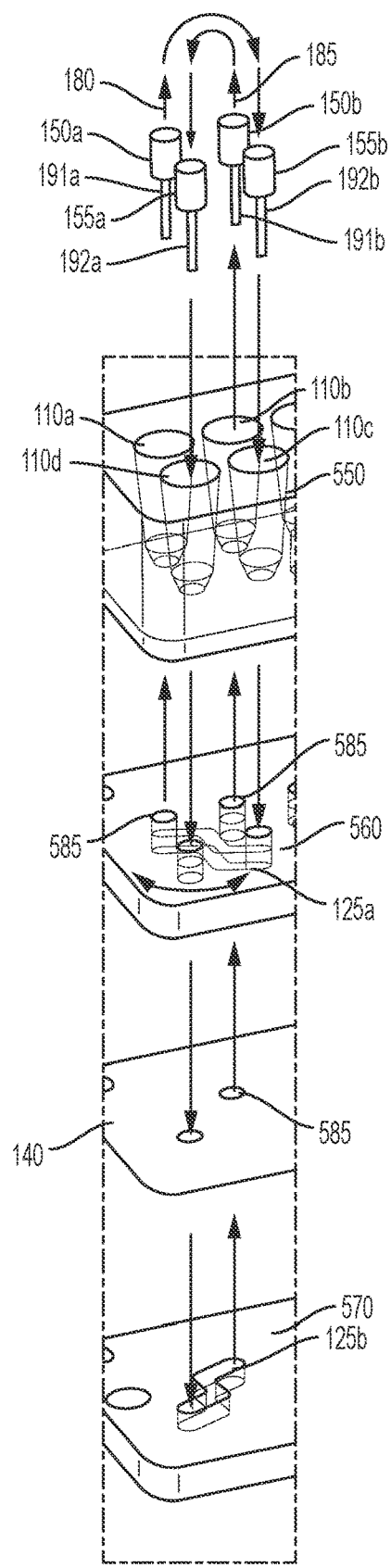
FIG. 5B illustrates fluid pathways through the structural layers of the example cell culture platform illustrated in FIG. 5A.

FIG. 5B illustrates fluid pathways through the structural layers of the example cell culture platform 105 illustrated in FIG. 5A. In FIG. 5B, a gravity fed fluid flow circulates through the tissue modeling environment by travelling through the first microchannel 125a. The first fluid reservoir 110a and the third fluid reservoir 110c are fluidically coupled by the first microchannel 125a defined in the underside of the second structural layer 560. When the first fluid reservoir 110a and the third fluid reservoir 110c each have a column of fluid of equal height, there is no gravity fed fluid flow through the first microchannel 125a. In order to create a difference in height between the columns of fluid in the first fluid reservoir 110a and the third fluid reservoir 110c, the pump assembly 115 pumps a first fluid 180 out of the second fluid output valve 155b into the third fluid reservoir 110c. Introducing the first fluid 180 into the third fluid reservoir 110c creates a difference in height between the columns of fluid in the first fluid reservoir 110a and the third fluid reservoir 110c causing a gravity fed fluid flow 180 from the first fluid reservoir 110c to the second structural layer 560. The fluid flow 180 enters the second structural layer 560 through a bore hole 585. The first fluid flow 180 travels across the first microchannel 125a defined in the second structural layer 560. The fluid flow 180 exits the first microchannel 125a and the second structural layer 560 via another bore hole 585. The first fluid flow 180 enters the first fluid reservoir 110a causing the fluid column height between the first fluid reservoir 110a and the third fluid reservoir 110c to equalize. Once the fluid column height between the first fluid reservoir 110a and the third fluid reservoir 110c equalizes, there will no longer be a gravity fed fluid flow through the first microchannel 125a. In order to maintain the gravity fed fluid flow 180 through first microchannel 125a, a difference in fluid column height between the first fluid reservoir 110a and the third fluid reservoir 110c needs to be maintained. Therefore, the pump assembly 115 pumps the first fluid 180 out of the first fluid reservoir 110a through the first fluid input valve 150a repeatedly creating a difference in fluid column height between the first fluid reservoir 110a and the third fluid reservoir 110c.

In FIG. 5B, a second gravity fed fluid flow circulates through the tissue modeling environment by travelling through the second microchannel 125b. The second fluid reservoir 110b and the fourth fluid reservoir 110d are fluidically coupled by the second microchannel 125b defined in the underside of the second structural layer 570. When the second fluid reservoir 110b and the fourth fluid reservoir 110d each have a column of fluid of equal height, there is no gravity fed fluid flow through the second microchannel 125b. In order to create a difference in height between the columns of fluid in the second fluid reservoir 110b and the fourth fluid reservoir 110d, the pump assembly 115 pumps a second fluid 185 out of the second fluid input valve 150b into the fourth fluid reservoir 110d. Introducing the second fluid 185 into the fourth fluid reservoir 110d creates a difference in height between the columns of fluid in the second fluid reservoir 110b and the fourth fluid reservoir 110*d* and causes the gravity fed second fluid flow 185 to travel from the second fluid reservoir 110*b* into the second structural layer 560. The second fluid flow 185 enters and exits the second structural layer 560 through a bore hole 585. The second fluid flow 185 enters and exits the membrane 140 through another bore hole 585 and travels across the second microchannel 125*b* defined in the third structural layer 570. The second fluid 185 exits the second microchannel 125*b* and travels through the second structural layer 560 via the bore hole 585. The first fluid flow 180 enters the second fluid reservoir 110*b* causing the fluid column height between the second fluid reservoir 110*b* and the fourth fluid reservoir 110*d* to equalize. Once the fluid column height between the second fluid reservoir 110*b* and the fourth fluid reservoir 110*d* equalizes, there will no longer be gravity fed fluid flow through the second microchannel 125*b*. In order to maintain the gravity fed fluid flow 185 through second microchannel 125*b*, a difference fluid column height between the second fluid reservoir 110*b* and the fourth fluid reservoir 110*d* needs to be maintained. Therefore, the pump assembly 115 pumps the second fluid 185 out of the second fluid reservoir 110*b* through the second fluid input valve 150*b* once again creating a difference in fluid column height between the second fluid reservoir 110*b* and the fourth fluid reservoir 110*d*. In some implementations, the first fluid 180 and the second fluid 185 recirculate within one tissue modeling environment.

In some implementations, the first fluid 180 and the second fluid 185 are not recirculated but are rather moved out of the tissue modeling environment by the pump assembly 115. In other implementations, the first fluid 180 and the second fluid 185 are moved between different tissue modeling environments. In other implementations, the first fluid 180 and the second fluid 185 are introduced to the fluid reservoirs 110*c* and 110*d* respectively from a fluid source outside the tissue modeling environment rather than being introduced from the fluid reservoirs 110*a* and 110*b*. In some implementations, the first fluid 180 and the second fluid 185 are drained to a fluid sink that resides outside the tissue modeling environment. In some implementations, the fluid source and the fluid sink may be one or more tissue modeling environments. In some implementations, multiple tissue modeling environments in the cell culture platform 105 may be interconnected. The flow rate with a tissue modeling environment may be changed by changing the pump rate, the input valve or output valve sipper depth, the pump chamber diaphragm size or the bore height. In some implementations, fluid flow through the first microchannel 125*a* above the membrane 140 and fluid flow through the second microchannel 125*b* below the membrane 140 can each produced by dedicated pump chambers, input and output valves, and fluid reservoirs to perfuse the first microchannel 125*a* and the second microchannel 125*b* independently of each other. In some implementations, the first microchannel 125*a* or the second microchannel 125*b* or both microchannels 125*a* and 125*b* may have a fluid flow rate of zero.

In some implementations, the cell culture platform 105 includes components configured to enable a biochemical reading via optical sensors, electrode traces or other biocompatible sensors. In some implementations, the sensors may be connected to external sensing hardware, which in turn may be coupled to the controller mentioned above. In some implementations, the sensors provide real-time and direct quantification of cell culture conditions and tissue response. Parameters such as tissue culture health, quality, morphology, confluence etc. can be monitored and evaluated without having to remove the cell culture platform 105 from an incubator. The optical sensors may have a fluorescence or phosphorescence that is modulated by the concentration of molecules of glucose, oxygen, or other analytes. The electrode trace may include silver chloride, gold, platinum or other biocompatible conductors. In some implementations, the electrodes are configured to stimulate and record electrical signals to, for example, generate a TransEpithelial Electrical Resistance (TEER) profile. TEER is used, in some implementations, to measure the integrity and health of the tissues cultured in the tissue modeling environment.

Figure 6B:
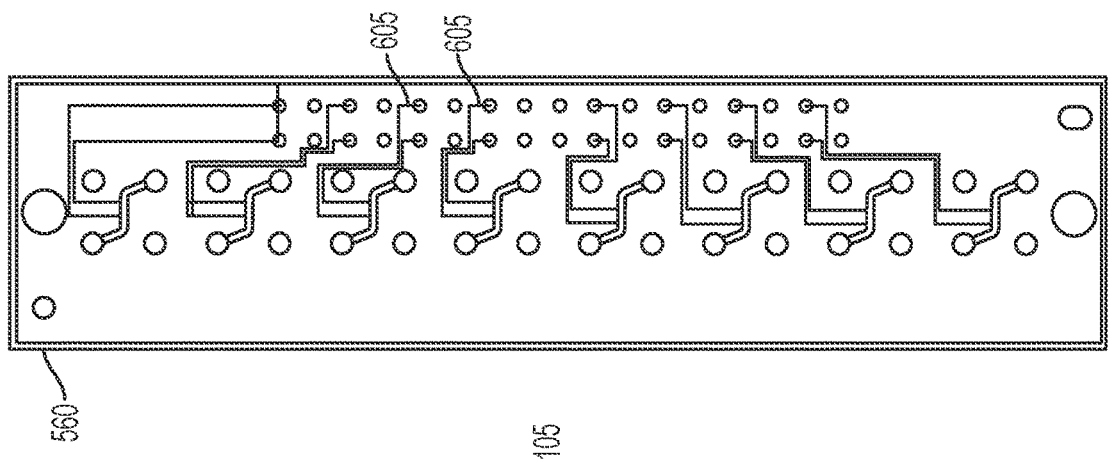
FIG. 6B illustrates a top down view of the second structural layer of the example cell culture platform illustrated in FIG. 6A.
Figure 6A:
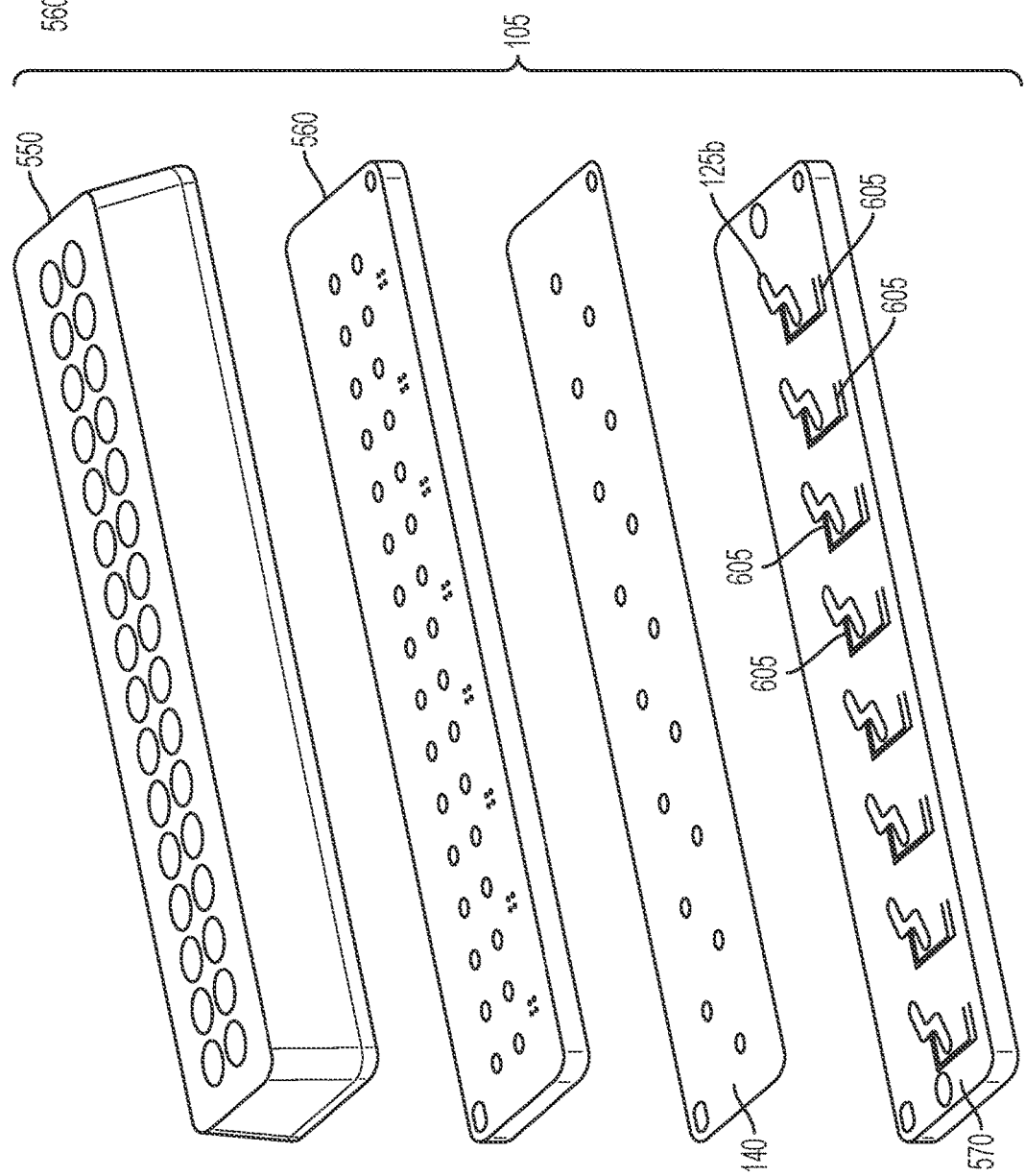
FIG. 6A illustrates an exploded view of an example cell culture platform having an array of tissue modeling environments with integrated sensors.

FIG. 6A illustrates an exploded view of an example cell culture platform 105 having an array of tissue modeling environments with integrated sensors. FIG. 6A, includes a first structural layer 550, a second structural layer 560, a membrane 140, and a third structural layer 570. The second structural layer 560 defines a first set of microchannel such as the first microchannel 125*a*. The third structural layer 570 defines a second set of microchannel structures, such as a second microchannel 125*b*. The third structural layer 570 includes an array of electrodes 605 with each microchannel such as the second microchannel 125*b* having two dedicated electrodes 605. In FIG. 6A, the array of electrodes 605 are printed onto the second set of microchannels 125*b* to make a continuous and conformal electric connection between the electrodes 605 in the microchannels 125*b* and external sensing hardware. FIG. 6B illustrates a top side down view of the second structural layer 560 of the example cell culture platform 105 illustrated in FIG. 6A. In some implementations, the electrode 605 may be electrode traces having a line width of about 100 microns.

Figure 6C:
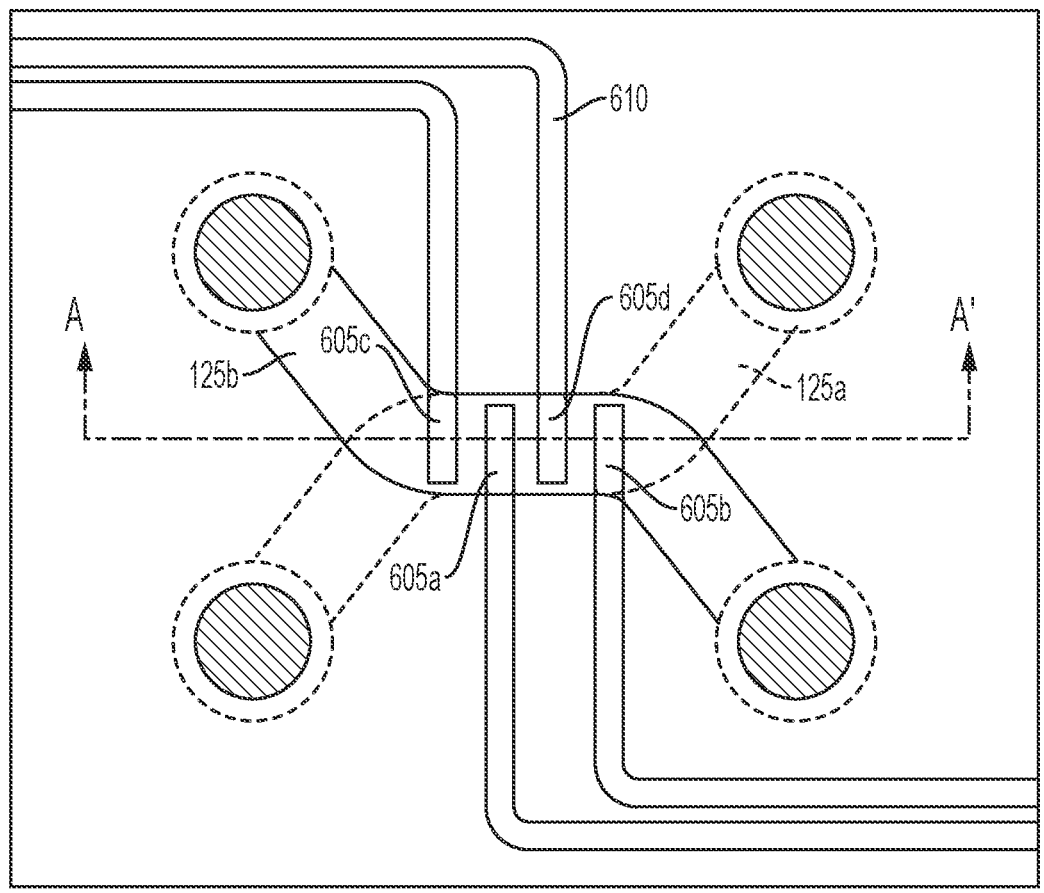
FIG. 6C illustrates an exploded view of an example cell culture platform having a single tissue modeling environment with integrated sensors.

FIG. 6C illustrates a top view of an example cell culture environment with integrated sensors. FIG. 6C is a top viewing looking down through the second structural layer and the third structural layer. In FIG. 6C, the cell culture platform includes a first microchannel 125*a*, a second microchannel 125*b*, a plurality of traces 610, and a plurality of electrodes 605. The cell culture environment includes an array of electrodes 605, such as a first electrode 605*a*, a second electrode 605*b*, a third electrode 605*c*, and a fourth electrode 605*d*. The electrodes 605 are routed to traces 610. The traces apply current and voltage to the electrodes 605 from current sources and voltage sources located outside the cell culture platform. The first electrode 605*a* and the second electrode 605*b* are printed onto the second microchannel 125*b* and the third electrode 605*c* and the fourth electrode 605*d* are printed on the first microchannel 125*a*.

Figure 6D:
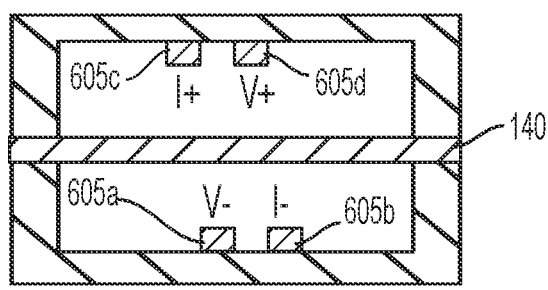
FIG. 6D illustrates a cross sectional view the example cell culture platform shown in FIG. 6C.

FIG. 6D illustrates a cross sectional view the cell culture platform shown by the line labeled A-A' in FIG. 6C. FIG. 6D includes a first microchannel 125*a*, a second microchannel 125*b*, a membrane 140, and a plurality of electrodes 605. The membrane separates the first microchannel and the second microchannel 125*b*. The first microchannel includes a third electrode 605*c* and a fourth electrode 605*d* and the second microchannel includes a first electrode 605*a* and a second electrode 605*b*.

In some implementations, the first microchannel 125*a* and the second microchannel 125*b* each include a pair of electrodes. In some implementations, only one of the first microchannel 125*a* and the second microchannel 125*b* includes electrodes. In some implementations, a single pair of electrodes is placed across the membrane 140 (i.e., one in each microchannel) may measure the electrochemical impedance of a cell layer across the membrane using electrochemical impedance spectroscopy to measure electrical resistance over a range of frequencies. In some implementations, a set of four electrodes may be used (i.e., two in each microchannel) as a four point probe to measure the response and impedance at a single frequency. In some implementations, a pair of electrodes may be placed in the first or second microchannel 125a or 125b and only one electrode may be place in the other microchannel and still serve as a four-point probe. In some implementations, the microchannel structure of a tissue modeling environment may be fabricated by embossing a plastic material.

Figure 7B:
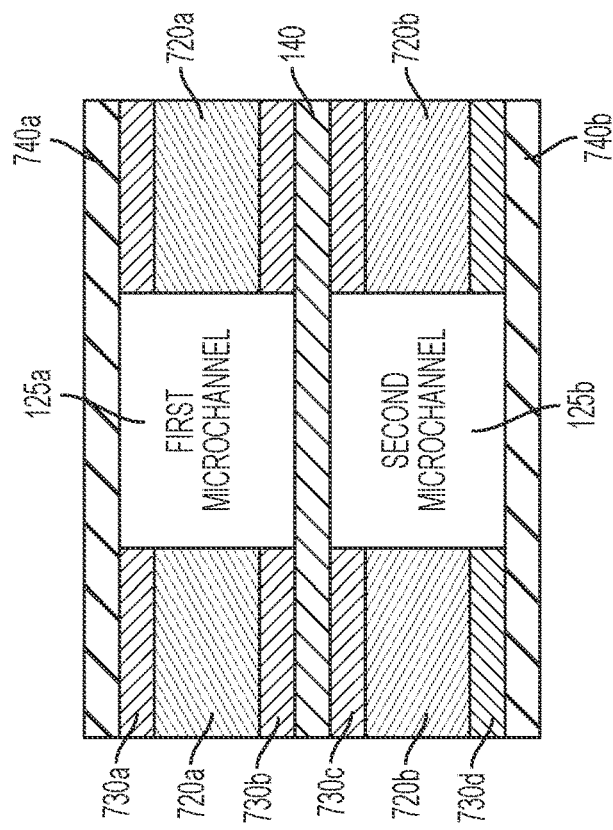
FIG. 7B illustrates a cross section of a microchannel structure fabricated using a thru cut technique.
Figure 7A:
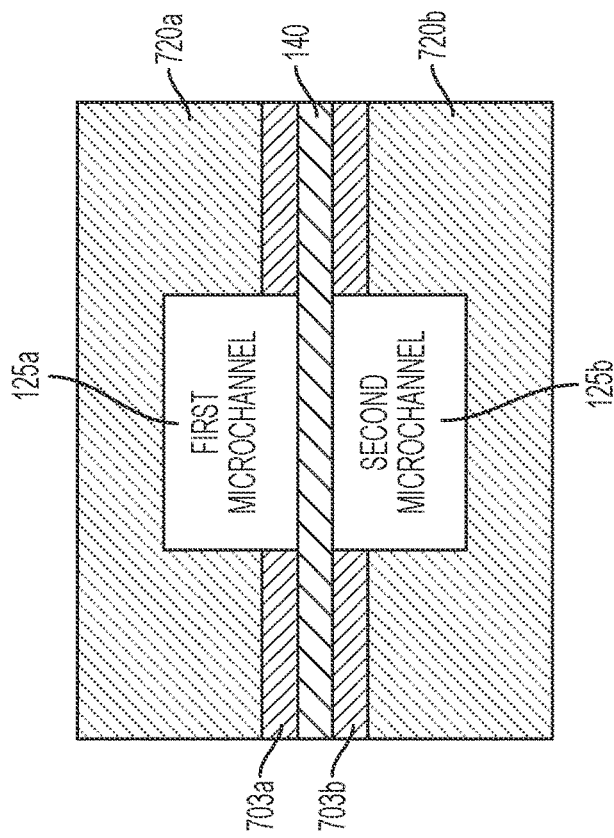
FIG. 7A illustrates a cross section of a microchannel structure fabricated by embossing a plastic material.

FIG. 7A illustrates a cross section of a microchannel structure fabricated by embossing a plastic material. In FIG. 7A, the microchannels 125 include a first piece of embossed plastic material 720a and a second piece of embossed plastic material 720b, a membrane 140, a first layer of adhesive film 730a and a second layer of adhesive film 730b. The first and second pieces of embossed plastic material 720a and 720b are each a plastic material embossed with a cavity in the form of a microchannel. The fabrication process includes attaching the first layer of adhesive film 730a to the first piece of embossed plastic material 720a and attaching the second layer of adhesive film 730b to the second piece of embossed plastic material 720b. Portions of the first and second layers of adhesive film 730a and 730b are cut out or removed around and inside the microchannels 125 and ports allowing fluid to flow through the ports and into the microchannels 125. The first and second layers of adhesive film 730a and 730b are attached to the membrane 140. In some implementations, the various components may be attached using thermal or pressure sensitive adhesives. In some implementations, the membrane 140 may manufactured from be a track-etched polycarbonate membrane. In some implementations, the first and second embossed plastic material 720a and 720b and the adhesive film 730 may be manufactured from cyclic olefin co-polymer (COC) or gas/oxygen permeable polymers such as fluorinated ethylene propylene (FEP) or polymethylpentene (PMP), polyurethane, polystyrene or polysufone. In some implementations of the fabrication process, portions of the membrane 140 may be plasma activated or exposed to UV through a photolithographic mask to create free radical and promoting the cells to adhere to the membrane 140. In some implementations in which the microchannel structure in a tissue modeling environment is fabricated using an embossed plastic material, a plurality of electrode sensors may be printed onto the various layers using 3-D printing techniques.

In some implementations, the microchannel structure of a tissue modeling environment may be fabricated using a thru-cut technique. FIG. 7B illustrates a cross section of a microchannel structure fabricated using a thru cut technique. In FIG. 7B, the microchannel structure includes a first layer of plastic material 720a, a second layer of plastic material 720b, a membrane 140, a first layer of adhesive film 730a, a second layer of adhesive film 730b, a third layer of adhesive film 730c, a fourth layer of adhesive film 730d, a first layer of thin film 740a and a second layer of thin film 740b. The fabrication process includes attaching the first layer of adhesive film 730a to a first side of the first plastic material 720a and attaching the second layer of adhesive film 730b to a second side of the first plastic material 720a. The fabrication process further includes attaching the third layer of adhesive film 730c to a first side of the second layer of plastic material 720b and attaching the fourth layer of adhesive film 730d to a second side of the second plastic material 720b. Portions of the first, second, third and fourth layers of adhesive film 730a-730d and portions of the first and second layers of plastic material 720a and 720b are cut out or removed from areas around and inside the microchannels 125 and ports allowing fluid to flow through the ports and into the microchannels 125. A first side of the membrane 140 is attached to portions of the second layer of adhesive film 730b and a second side of the membrane 140 is attached to portions of the third layer of adhesive film 730c. The microchannel structure is stabilized by adhering a first layer of thin film 740a to the first layer of adhesive film 730a and adhering a second layer of thin film 740a to the fourth layer of adhesive film 730d.

Figure 8:
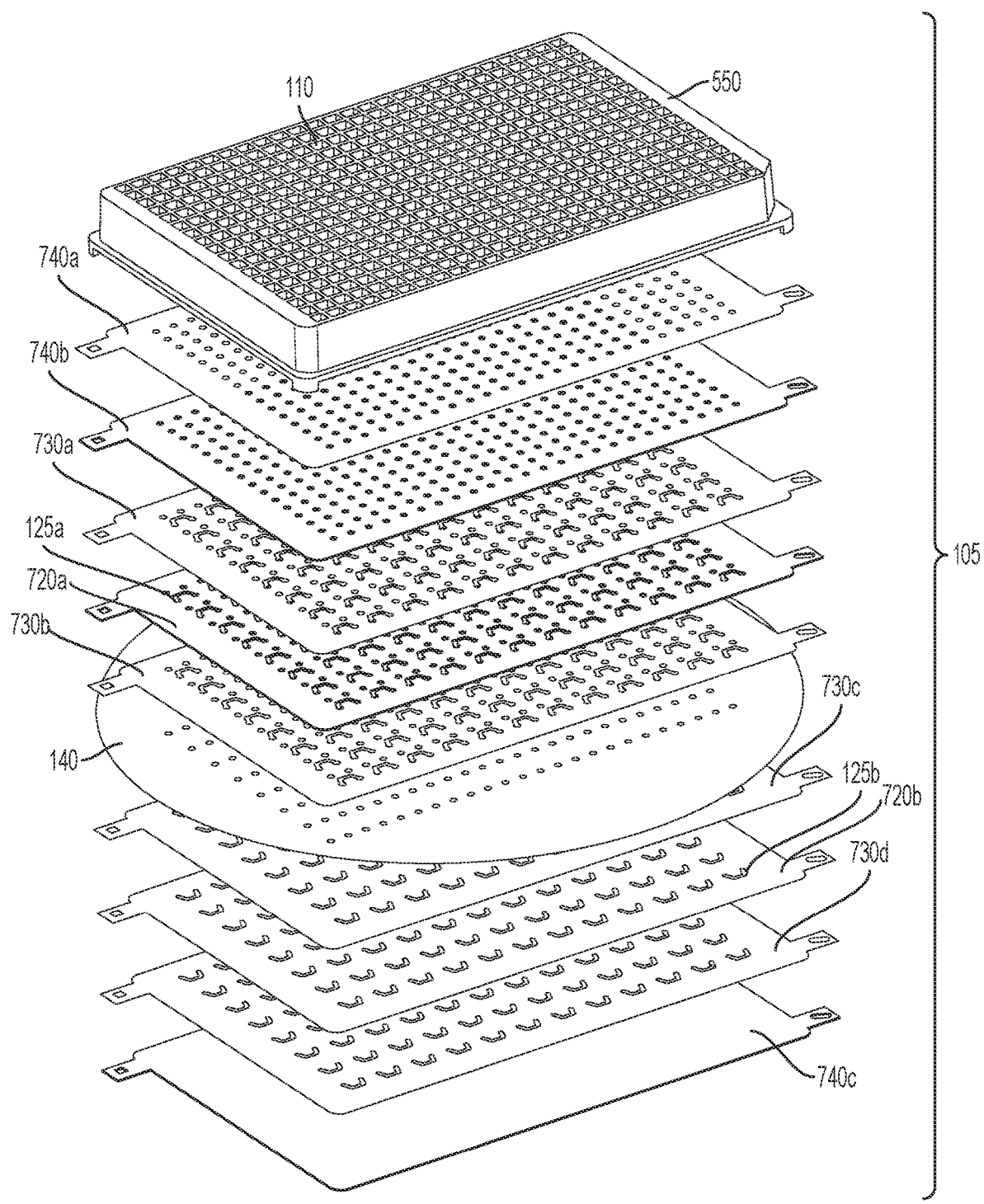
FIG. 8 illustrates an exploded view of an example cell culture platform fabricated using a thru cut technique, as previously shown in FIG. 7B.

FIG. 8 illustrates an exploded view of an example cell culture platform fabricated using a thru-cut technique, as previously shown in FIG. 7B. An array of tissue modeling environments in a cell culture platform is defined by several structural layers separated by a membrane 140. In FIG. 8 the microchannel structure includes a first layer of plastic material 720a and a second layer of plastic material 720b, a first layer of adhesive film 730a, a second layer of adhesive film 730b, a third layer of adhesive film 730c, and a fourth layer of adhesive film 730d, a first layer of thin film 740a, a second layer of thin film 740b, and a third layer of thin film 740c. FIG. 8 also includes a membrane 140, microchannel structures 125a and 125b, a first structural layer 550, and a plurality of fluid reservoirs 110. The first microchannel 125a is formed by a cut through in the first layer of adhesive film 730a, the first layer of plastic material 720a, and the second layer of adhesive film 730b. The second microchannel 125 is formed by a cut through in the third layer of adhesive film 730c, the first layer of plastic material 720b, and forth layer adhesive film 730d.

The fabrication of the cell culture platform includes attaching the first structural layer 550 to the first layer of thin film 740a. It further includes attaching the second layer of thin film 740b to the second side of the first layer of thin film 740a and to the first side of the first layer of adhesive film 730a. Fabrication further includes attaching the second side of the first layer of adhesive film 730a to the first layer of plastic material 720a. Fabrication further includes attaching the second side of the first plastic material 720a to the second layer of adhesive film 730b. The first side of the membrane 140 attaches to portions of the second layer of adhesive film 730b and to portions of the third layer of adhesive film 730c. The third layer of adhesive film 730d attaches to the second layer of plastic material 720b and the second side of the second layer of plastic material attaches to the fourth layer of adhesive film 730d. The second side of the fourth layer of adhesive film 730d attaches to the third layer of thin film 740c. The first layer of thin film 740a, the second layer of thin film 740b, and the third layer of thin film 740c provide stabilization to the microchannel structure 125. In some implementations, the adhesive film may be manufactured from an epoxy or curable adhesive. In some implementations, the adhesive film may be manufactured from an adhesive tape such as a pressure sensitive adhesive. In some implementations, the adhesive film may be manufactured from a material that has been fluoroetched, plasma treated, chemically etched, or surface patterned to enhance its adhesive properties. In some implementations, the adhesive film may be the same class of polymer as the plastic material but with a different melting point or glass transition temperature. In some implementations, the adhesive film may be about 1.0 to 25 μm thick.

In some implementations, the various components may be attached using thermal or pressure sensitive adhesives. In some implementations, the membrane 140 may be manufactured from a track-etched polycarbonate membrane. In some implementations, the first and second layer of plastic material 720a and 720b, the first, second, third and fourth layer of adhesive film 730a-730d and the first, second, and third layer of thin film 740a, 740b, and 740c, respectively, may be manufactured from COC or gas/oxygen permeable polymers such as fluorinated ethylene propylene (FEP) or polymethylpentene (PMP), polyurethane, polystyrene or polysufone. In some implementations, the third layer of thin film 740c may be manufactured from an oxygen permeable material such as FEP which may allow fluid flow to be decoupled from oxygen requirements, or enable static cell cultures where there is no flow in either microchannel. In some implementations, the third layer of thin film 740c may be manufactured from an oxygen impermeable material in order to control the oxygen environment through the fluid flow or lack thereof and create hypoxic conditions. In some implementations in which the microchannel structure in a tissue modeling environment is fabricated using a thru cut technique, a plurality of electrode sensors may be formed using lithography.

Referring to FIGS. 1-10, FIG. 11 illustrates a flow chart of an example method 1000 for populating cells into the cell culture platform. The method 1000 includes providing a cell culture platform and a plurality of cells (step 1001). Then, a first cell type is seeded into a first microchannel structure and a second cell type is seeded into a second microchannel structure (step 1002). Next, the method 1000 includes applying a first feeder flow to the first cells (step 1003). Then, applying a second feeder flow to the second cells (step 1004). Experiments may be conducted across the populated cells in the cell culture platform (step 1005).

As set forth above, the method 1000 begins with the provision of a cell culture platform including a plurality of tissue modeling environments and a plurality of cells (step 1001). In some implementations, the tissue modeling environments may be similar to the tissue modeling environments described in FIG. 1-10 above. For example, the tissue modeling environment includes a group of fluid reservoirs 110 fluidically coupled by a pair of microchannel structures 125, including a first microchannel 125a and a second microchannel 125b separated by a membrane 140, as shown in FIG. 3A and FIG. 3B. The tissue modeling environments can be arrayed in a cell culture platform such as the platform 105 shown in FIG. 1.

A first cell type is seeded into the first microchannel 125a while a second cell type is seeded into the second microchannel 125b (step 1002). In some implementations, the first microchannel structure 125b represents an apical channel and the second microchannel structure represents a basal channel. In some implementations, the first cell type may be epithelial cells and the second cell type may be microvascular cells. In other implementations, the cell culture platform may approximate the in vivo structure of a renal tubule, where the first cell type may be renal proximal epithelial cells and the second cell type may be endothelial cells. The cells can be seeded into the respective channels by disposing the cells into reservoirs of the respective cell tissue culture environments, and allowing the cells to flow through the microchannels and the pump assembly as fluid is extracted from outlet reservoirs and reintroduced into inlet reservoirs of the tissue culture environments until the cells adhere to the membrane in the microchannels.

A first feeder flow is applied to the first cell type in the first microchannel 125a (step 1003). In some implementations, the feeder flow is applied to the cells at a rate of about 1 µL/min. In other implementations, the feeder flow is applied to the first cells at a rate less than 1 µL/min. The first feeder flow can include cell culture media typically used for culturing cells. In some implementations, the first feeder flow can include a proliferative cell culture medium. In some implementations, the first feeder flow can include several components or supplements of cell culture medias, mixed to create an environment conducive for growth, differentiation, or survival of multiple cell types. In some implementations, the first feeder flow may be a buffer or saline solution.

A second feeder flow is applied to the second cell type in the second microchannel 125b (step 1004). In some implementations, the second feeder flow is applied to the second cell type about 24 hours after the first feeder flow was applied to the first cell type. In some implementations, feeder flow is applied to the second cell type at a rate of about 1 µL/min. The second feeder flow can include cell culture media typically used for culturing cells. In some implementations, the second feeder flow can include can include a proliferative cell culture medium. In some implementations, the second feeder flow can include several components or supplements of cell culture medias, mixed to create an environment conducive for growth, differentiation, or survival of multiple cell types. In some implementations, the second feeder flow may be a buffer or saline solution. In some implementations, the fluid flow can be used to condition cells, maintain cell growth, differentiate cells, profuse the tissue, seed cells, and/or administer mechanical stresses and forces.

The first microchannel 125a can have a first fluid flow and the second microchannel 125b can have a second fluid flow. In some implementations, the first microchannel 125a and the second microchannel 125b can have the same flow rate. In some implementations, after the cells have been cultured in their respective microchannels 125a and 125b for an initial amount of time (e.g., about 24-48 hours), the pump rate may increase to about 1 µL/sec in both the first microchannel 125a and the second 125b structure to mimic physiological shear stress on the cells. In some implementations, the first flow rate or the second flow rate may increase to a rate which exerts about 0.1 Pa of pressure across the cell membrane 140, thereby mimicking a kidney proximal tubule.

The method 1000 further includes conducting experiments upon the cells in the culture platform. In some implementations, the experiment may measure barrier function across the cell membrane over the course of several days. In some implementations, the experiment may calculate the rate of transport across the membrane 140. In some implementations, the cell culture platform mimics an organ system by introducing a plurality of molecules to a specific cell type on the membrane 140 and the experiment measures transport. For example, a user may combine a liquid-gas molecule into a cell culture platform configured with alveolar cells on the membrane to measure real-time transport in the lungs. In some implementations, a user may couple multiple tissue modeling environments with different cell types to mimic a plurality of organ systems. In some implementations, the plurality of molecules may represent a specific drug and the experiment provides a drug to tissue delivery analysis. In some other implementations, biologically active agents, such as a drugs, toxins, chemotherapeutics, nutrients, bacteria, viral particles, etc., are pumped through the cell culture environments at the same or different concentrations and/or flow rates to measure the impact of such agents on the cell culture environments.

Referring to FIGS. 1-10, FIG. 12 illustrates a flow chart of an example experimental method 2000 for simulating hypoxic conditions in healthy tissue. In some implementations, the cell culture platform controls oxygen levels in one or more channels to mimic hypoxic conditions in healthy tissue, such as the gut microenvironment, disease states, or ischemia in the kidneys. The method 2000 includes populating a cell culture platform with a plurality of cells (step 2002), as shown in example method 1000 above. Then, the method 2000 includes applying a feeder flow into a first microchannel structure and a feeder flow into a second microchannel structure (step 2002). Method 2000 includes measuring the tissue structure across the cell membrane (step 2003). The feeder flow is varied in the first microchannel structure and the second microchannel structure to replicate hypoxic conditions (step 2004). The method 2000 further includes measuring changes in the tissue structure across the cell membrane (step 2005) due to the replicated hypoxic condition.

As set forth above, the method 2000 begins with populating a cell culture platform with a plurality of cells (step 2001), similar to example method 1000 above. In some implementations, the cell culture platform can be similar to cell culture platforms 105 described in FIG. 1-10. For example, the cell culture platform may include a first microchannel 125*a*, a second microchannel 125*b*, a membrane 140 separating the first microchannel 125*a* and the second microchannel 125*b*, and a group of fluid reservoirs 110 fluidically coupled by the first microchannel structure 125*a* and the second microchannel structure 125*b*, as shown in FIG. 3A and FIG. 3B. Multiple cell culture environments can be arrayed across the cell culture platform, e.g., with the reservoirs of the cell culture environments having an arrangement similar to a standard well plate arrangement. In some implementations, the first and the second microchannel structures may be formed in a gas-impermeable polymer.

Next, the method 2000 includes applying a first feeder flow into a first microchannel 125*a* and a second feeder flow into a second microchannel 125*a* (step 2002). In some implementations, the pump assembly 115, similar to FIG. 5A, applies the feeder flow to the cells at a rate greater than to keep the oxygen levels of the cells high. Then, method 2000 includes measuring the tissue structure across the cell membrane (step 2003). For example, TEER measurements can be made across the cells coupled to the cell membrane.

Next, the method 2000 includes varying the feeder flow in the first microchannel 125*a* as well as varying the feeder flow in the second microchannel 125*b* to replicate a hypoxic condition (step 2004). In some implementations, the pump assembly 115 varies the flow rate to less than 1 μL/min in order to lower the oxygen levels in the cells. In other implementations, low oxygen content fluid can be delivered at a suitable flow rate. In other implementations, the top of the fluid reservoirs 110 may be blocked to limit the introduction of environmental oxygen into the fluid flows and thus to the cells. Next, step 2005 includes measuring changes in the tissue structure or, e.g., the TEER response of the cells, in response to the varying oxygen levels.

While this specification contains many specific implementation details, these should not be construed as limitations on the scope of any inventions or of what may be claimed, but rather as descriptions of features specific to particular implementations of particular inventions. Certain features that are described in this specification, in the context of separate implementations, can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described components and systems can generally be integrated together in a single product or packaged into multiple products.

References to "or" may be construed as inclusive so that any terms described using "or" may indicate any of a single, more than one, and all of the described terms. The labels "first," "second," "third," and so forth are not necessarily meant to indicate an ordering and are generally used merely to distinguish between like or similar items or elements. Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

What is claimed is:
1. An apparatus comprising:
a well plate comprising a plurality of structural layers, and a membrane, wherein the membrane separates two structural layers, and the well plate defines an array of tissue modeling environments, and each tissue modeling environment includes:
a first fluid reservoir, a second fluid reservoir, a third fluid reservoir and a fourth fluid reservoir, each fluid reservoir configured to hold a column of fluid;
a first microchannel fluidically coupling the first fluid reservoir to the second fluid reservoir;
a second microchannel fluidically coupling the third fluid reservoir to the fourth fluid reservoir, wherein at least a portion of the first microchannel overlaps at least a portion of the second microchannel across the membrane; and
a pump assembly configured to induce a first set of fluid flows through a first set of tissue modeling environments in the array of tissue modeling environments and to induce a second set of fluid flows through the first set of tissue modeling environments in the array of tissue modeling environments;
wherein the pump assembly the pump assembly is arranged above the well plate and further comprises, for each tissue modeling environment in the first set of tissue modeling environments:
a first output extending down from the pump assembly into the first fluid reservoir for pumping a first fluid into the first fluid reservoir;
a first intake extending down from the pump assembly into the second fluid reservoir for pumping the first fluid out of the second fluid reservoir;
a second output extending down from the pump assembly into the third fluid reservoir for pumping a second fluid into the third fluid reservoir; and a second intake extending down from the pump assembly into the fourth fluid reservoir for pumping the second fluid out of the fourth fluid reservoir.

2. A method for modeling tissue environments, the method comprising:
provliding the apparatus of claim 1,
seeding respective first cell types into the first microchannel of each tissue modeling environment,
operating the pump assembly to induce the first set of fluid flows through the first microchannel of each tissue modeling environment to expose the first cell types to the first set of fluid flows, and
operating the pump assembly to induce the second set of fluid flows through the second microchannel of each tissue modeling environment.

3. The method of claim 2, further comprising:
evaluating the respective seeded first cell types during and/or after application of the first and second sets of fluid flows.

4. The method of claim 2, further comprising:
seeding respective second cell types into the second microchannel of each tissue modeling environment, wherein inducing the second set of fluid flows through the second microchannel of each tissue modeling environment exposes the second cell types to the second set of fluid flows.

5. The method of claim 4, wherein the first cell types comprises epithelial cells and the second cell types comprises microvascular cells.

6. The method of claim 2, wherein the first set fluid flows have flow rates different than the flow rates of the flows in the second set of fluid flows.

7. The method of claim 2, comprising introducing a biologically active agent to the array of tissue modeling environments, and measuring the effect of the introduction of the biologically active agent on the first type of cells.

8. The method of claim 7, wherein introducing the biologically active agent to the array of tissue modeling environments comprises introducing different amounts of the biologically active agent into at least two of the tissue modeling environments.

9. The method of claim 7, wherein measuring the effect of the introduction of the biologically active agent on the first type of cells comprises measuring the effects of the introduction of biologically active agent in different ones of the plurality of tissue modeling environments having different fluid flow rates.

10. The method of claim 2, further comprising:
altering a fluid flow rate through one of the first and second microchannels of at least one the tissue modeling environments to replicate a hypoxic condition in the at least one tissue modeling environment; and
measuring the impact of the replicated hypoxic condition on the first cell types in the at least one tissue modeling environment.

11. The method of claim 2, wherein the first or second intake of the pump assembly for at least one tissue modeling environment is coupled to the first or second output of the pump assembly for a different tissue modeling environment.

12. The method of claim 2, further comprising measuring the first cell types using a sensor incorporated into each of the tissue modeling environments.

13. The method of claim 2, wherein the fluid reservoirs of the array of tissue modeling environments are arranged to correspond to the arrangement of wells of a standard well plate.

* * * * *